(12) United States Patent
Froom

(10) Patent No.: US 6,949,077 B2
(45) Date of Patent: Sep. 27, 2005

(54) ANTISPASTICITY AID DEVICE AND RELATED ACCESSORIES

(76) Inventor: Robert K. Froom, 18115 LaSalle Ave., Gardena, CA (US) 90248

( * ) Notice: Subject to any disclaimer, the term of this patent is extended or adjusted under 35 U.S.C. 154(b) by 20 days.

(21) Appl. No.: 10/712,968

(22) Filed: Nov. 12, 2003

(65) Prior Publication Data
US 2005/0101897 A1 May 12, 2005

(51) Int. Cl.$^7$ .................................................. A61F 5/00
(52) U.S. Cl. ........................ 602/21; 602/22; 128/878; 128/879; 128/880
(58) Field of Search ................................. 128/880, 878, 128/879; 602/21, 22

(56) References Cited

U.S. PATENT DOCUMENTS

| | | | |
|---|---|---|---|
| 1,220,476 A | | 3/1917 | Ujdur |
| 3,198,197 A | | 8/1965 | VanHalanger |
| 3,707,963 A | | 1/1973 | Keropian |
| 3,762,401 A | | 10/1973 | Tupper |
| 3,818,905 A | | 6/1974 | Lebold |
| 4,384,571 A | * | 5/1983 | Nuzzo et al. .................. 602/22 |
| 4,576,351 A | * | 3/1986 | Brink .......................... 248/118 |
| 4,782,825 A | * | 11/1988 | Lonardo ....................... 602/21 |
| 4,960,114 A | * | 10/1990 | Dale ............................ 602/21 |
| 5,060,638 A | * | 10/1991 | Bodine, Jr. ................... 602/21 |
| 5,121,743 A | | 6/1992 | Bishop |
| 5,140,998 A | | 8/1992 | Vickers |
| 5,456,650 A | | 10/1995 | Williams, Jr. et al. |
| 5,476,439 A | | 12/1995 | Robinson |
| 5,697,103 A | | 12/1997 | Wiggins |
| 5,718,671 A | * | 2/1998 | Bzoch ........................... 602/20 |
| 5,921,945 A | | 7/1999 | Gray |
| 6,010,473 A | | 1/2000 | Robinson |
| 6,094,756 A | * | 8/2000 | Carter ......................... 4/578.1 |
| 6,165,148 A | * | 12/2000 | Carr-Stock ................... 602/21 |
| 6,443,918 B1 | * | 9/2002 | Wang ............................ 602/5 |
| 6,482,168 B1 | | 11/2002 | Betcher |
| 6,561,995 B1 | | 5/2003 | Thibodo, Jr. |
| 6,692,453 B2 | * | 2/2004 | Wolfe .......................... 602/21 |

* cited by examiner

Primary Examiner—Henry Bennett
Assistant Examiner—Dinnatia Doster-Greene
(74) Attorney, Agent, or Firm—David A. Belasco; Belasco Jacobs & Townsley, LLP

(57) ABSTRACT

An antispasticity aid device designed to aid stroke victims. The invention is a hand brace constructed to hold the thumb and fingers flat and a series of accessories designed to re-educate the muscles after a stroke. The device has a hand-mounting and thumb-mounting member. First and second restraining straps hold the hand and thumb firmly in contact with the hand-mounting and thumb-mounting member, respectively. Accessories for use with the device include: A first accessory fitting on an arm of an armchair; a second accessory providing physical therapy; a third accessory maintaining a comfortable position to rest an arm; a fourth accessory fitting frictionally over the arm of a chair; a fifth accessory accepting the mounting bracket of the device; a sixth accessory suspending the arm; a seventh accessory providing a channel for resting an arm; an eighth accessory providing exercise for arm muscles; and a ninth accessory permitting physical therapy.

73 Claims, 15 Drawing Sheets

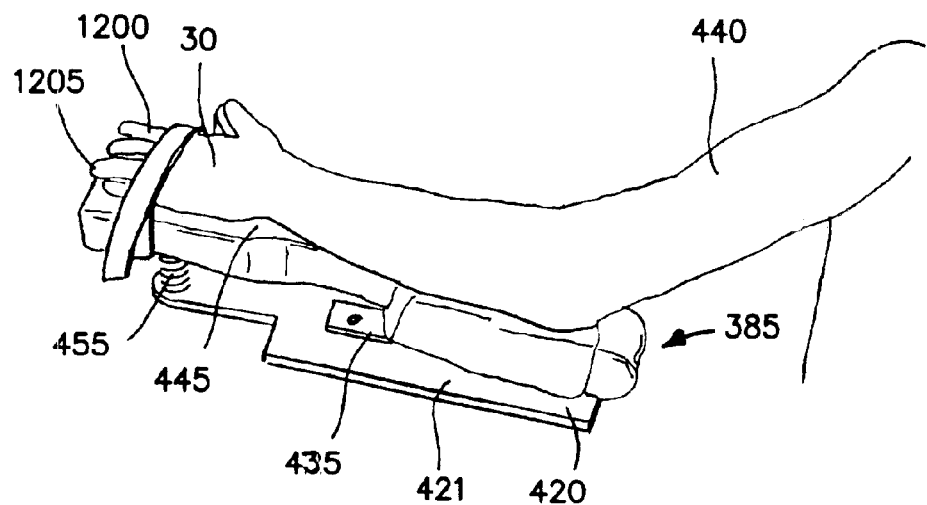
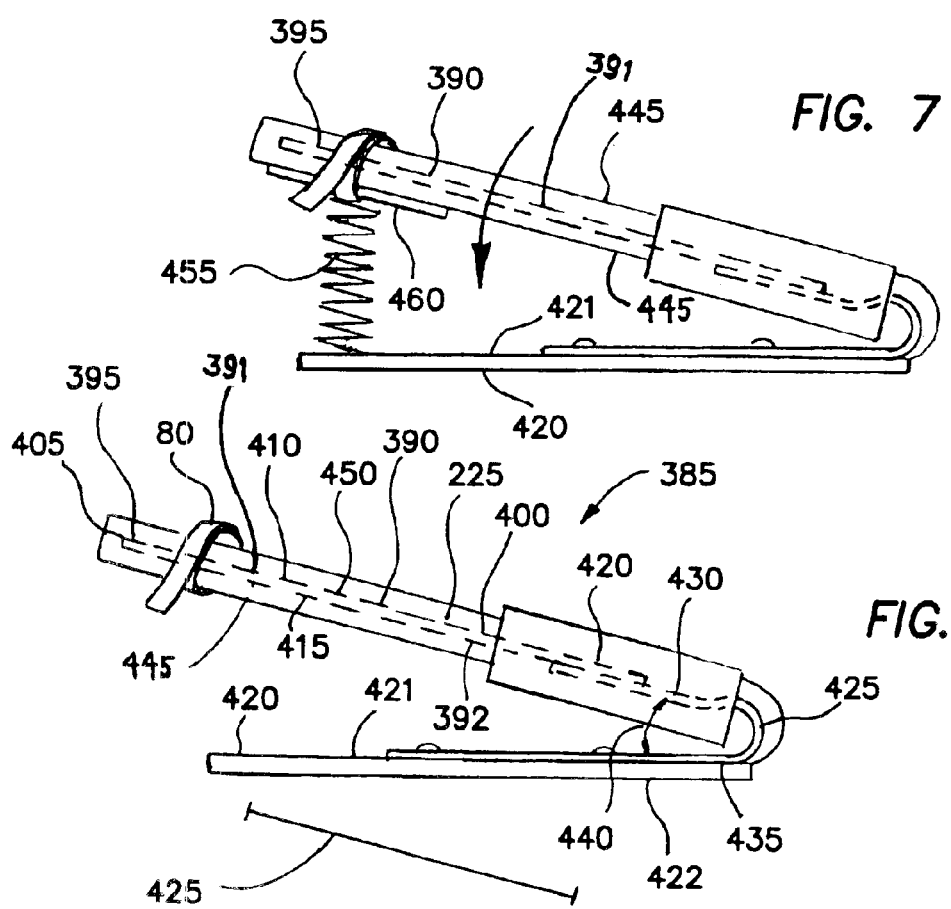

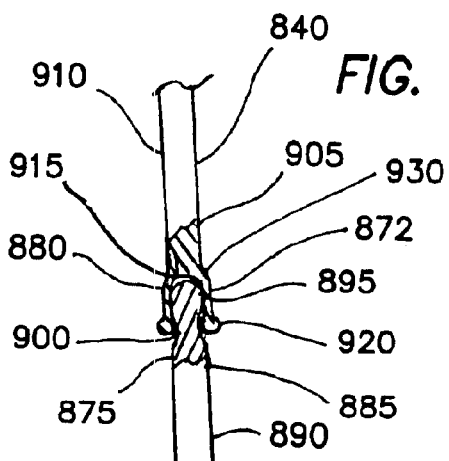
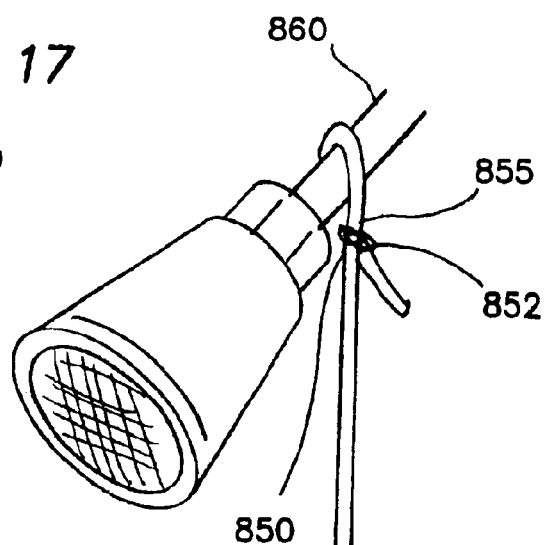
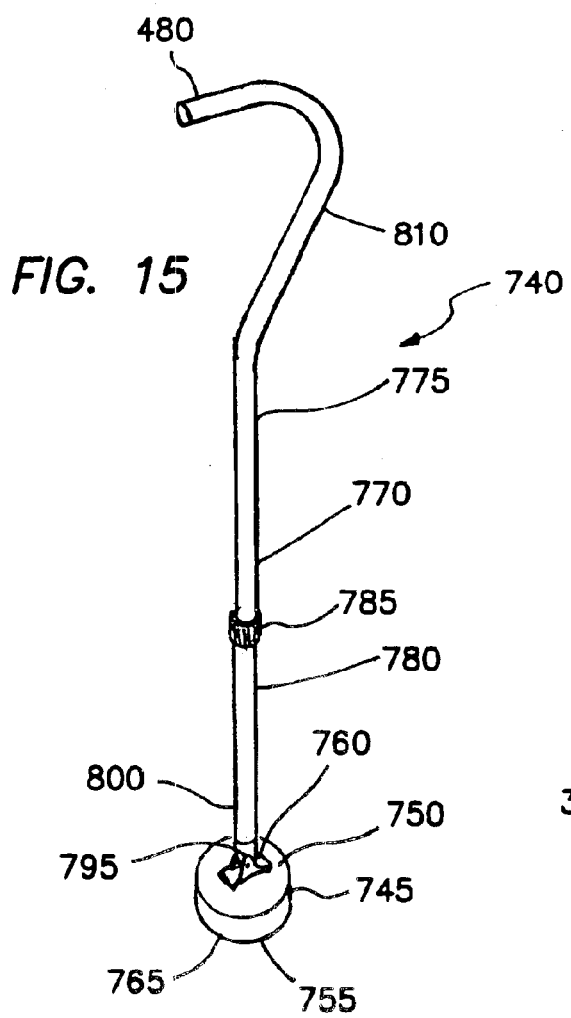
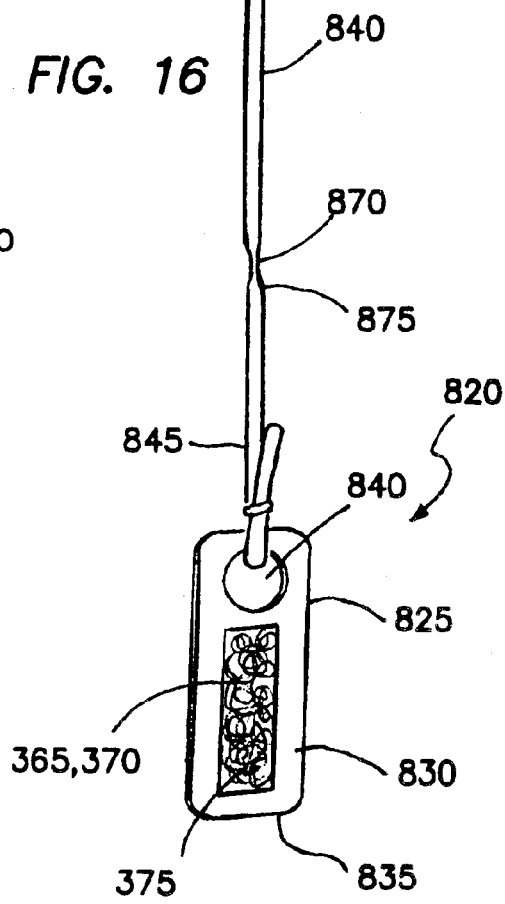
FIG. 17
FIG. 16
FIG. 15

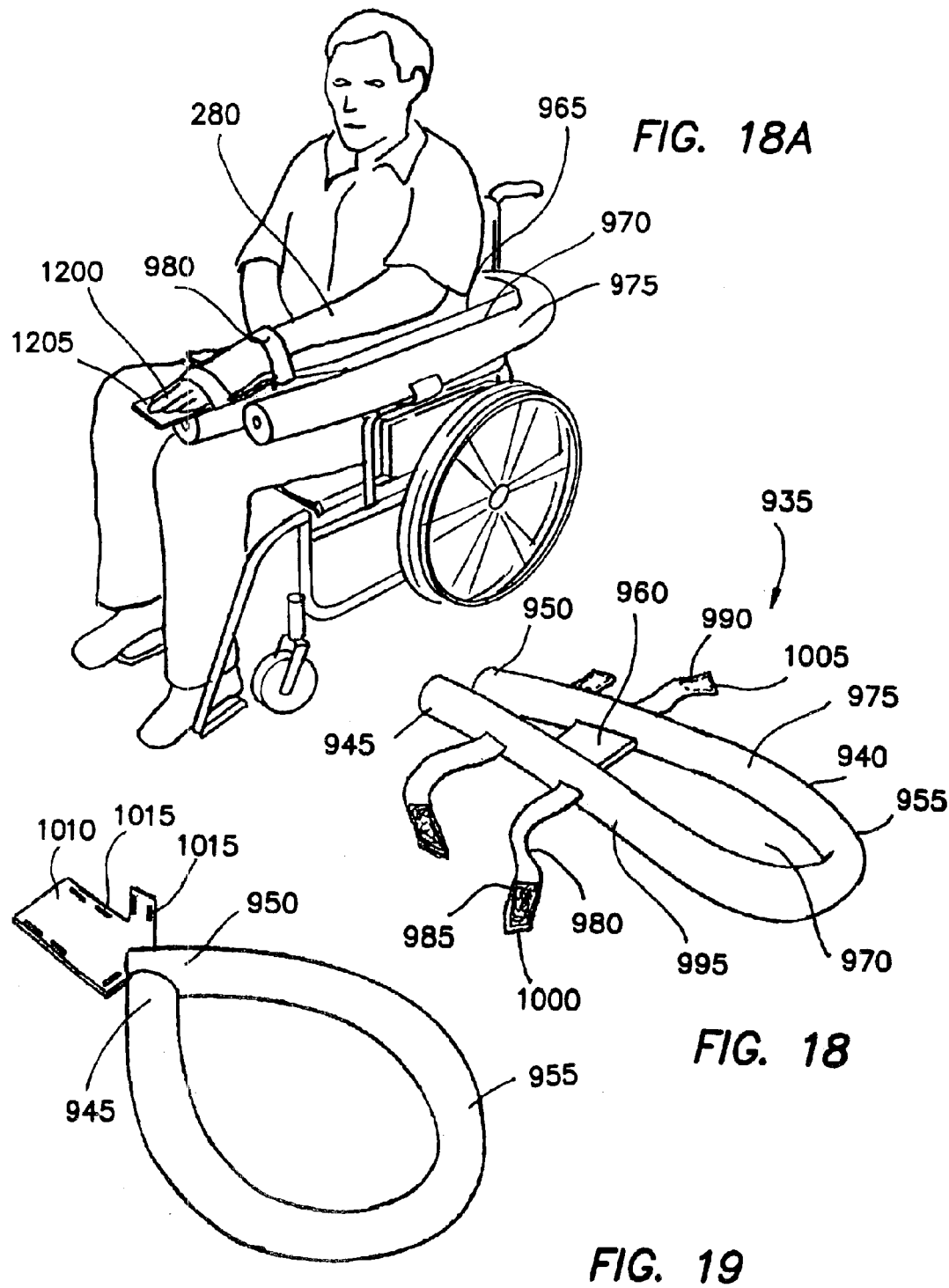

ANTISPASTICITY AID DEVICE AND RELATED ACCESSORIES

FIELD OF INVENTION

The invention pertains to devices designed to aid stroke victims and others suffering from spasticity. More particularly, the invention relates to a hand brace constructed to hold the thumb and fingers in a flattened arrangement and a series of devices designed to aid in the re-education of a stroke victim's muscles after a stroke.

BACKGROUND OF THE INVENTION

Various devices have been developed to provide comfort and assist in the rehabilitation of those suffering from spasticity of the hand muscles. In order to prevent cramping, nerve damage and possible muscle atrophy, it is often desirable to maintain the patient's hand in a planar orientation. Toward this end, many splint-like devices have been developed. None of the devices so far developed provide adjustments for radial orientation of the patient's thumb.

U.S. Pat. No. 5,121,743 issued to Bishop is directed to a hand-restraining device made of a rigid material. The hand-restraining device consists of a support member and a series of restraining straps used to secure a hand through the front surface of the support. A rigid knuckle-restraining piece on one of the straps is used to prevent bending of the knuckles. Two thumb/baby finger portions are included and the rear portion is extended to engage the forearm of the user.

U.S. Pat. No. 3,707,963 issued to Keropian, discloses an articulated hand brace. Here, a very complex articulated thumb guide is pivotally coupled to a portion of a hand support.

U.S. Pat. No. 6,482,168, issued to Betcher is directed to an upper extremity hand orthosis and method of use. The hand orthosis has a palm area in which a hand is positioned for support of a patient's fingers and right or left thumb in a spaced apart configuration. Two separate pairs of overlapping and connectable straps are positioned to encircle the hand, wrist and fingers of the user to keep movement to a minimum.

U.S. Pat. No. 5,921,945, issued to Gray is directed to a splint/therapeutic device. The splint can restrict a user's hand to a desired body position and provide a pre-selected degree of mobility, such as preventing the fingers of the hand from curling toward the wrist. Various straps and hook-and-loop type fasteners may be used as needed.

U.S. Pat. No. 6,561,995, issued to Thibodo, Jr. is directed to a splint system for two or more adjacent fingers of the hand. The splint can be used for maintaining the fingers in a straight line.

U.S. Pat. No. 3,762,401, issued to Tupper is directed to a surgical retractor. A hand is positioned on a thin flat paddle-shaped pallet such that the fingers lie on the pallet between pairs of elongated slots, with the wrist lying between another pair of elongated slots such that, with the use of elastic finger bands and wrist bands, the hand is held in place and flexing of the fingers is prevented.

While other variations exist, the above described designs for hand supports and splints are typical of those encountered in the prior art. It is an objective of the present invention to provide a hand support for spasticity victims that maintains the hand in a planar orientation. It is a further objective to provide a support that is comfortable for the spasticity victim to wear and is easily installed and removed.

It is a still further objective of the invention to provide the above-described capabilities in an inexpensive and durable support that may be easily cleaned and is light in weight. It is yet a further objective to provide a series of accessories for use with the support that will encourage retraining of the muscles of the spasticity victim's hand and arm.

While some of the objectives of the present invention are disclosed in the prior art, none of the inventions found include all of the requirements identified.

SUMMARY OF THE INVENTION

The present invention addresses all of the deficiencies or prior stroke victim aid inventions and satisfies all of the objectives described above.

(1) An antispasticity aid device providing the desired features may be constructed from the following components. A planar hand-mounting member is provided. The planar hand-mounting member is formed of rigid material and is sized and shaped to extend beyond the outer dimensions of a human hand without a thumb. The planar hand-mounting member has an upper surface, a lower surface, a front edge, a rear edge, a first side edge and a second side edge. The hand-mounting member has at least two first fastening slots located adjacent to the first and second side edges, respectively. A first restraining strap is provided. The first restraining strap is size and shaped to fit slidably through the first fastening slots and has a means for adjusting a length of the first strap. A thumb-mounting member is provided. The thumb-mounting member is formed of rigid material and is sized and shaped to extend beyond the outer dimensions of a human thumb. The thumb-mounting member has an upper surface, a lower surface, a front edge, a rear edge, a first side edge and a second side edge. The thumb-mounting member has at least two second fastening slots located adjacent to the first and the second side edges of the thumb-mounting member, respectively. A second restraining strap is provided. The second strap is sized and shaped to fit slidably through the second fastening slots and has a means for adjusting a length of the second strap. The thumb-mounting member is rotatably attached at its rear edge to the first side edge of the hand-mounting member. This permits the thumb-mounting member to rotate through an arc in the plane of the hand-mounting member whereby, when a hand of a stroke victim is placed upon the hand-mounting member, the first restraining strap is located over the hand and through the first fastening slots. The length of the first restraining strap is adjusted to hold the hand in firm contact with the hand-mounting member and when a thumb of a stroke victim is placed upon the thumb-mounting member, the second restraining strap is located over the thumb and through the second fastening slots. The length of the second restraining strap is adjusted to hold the thumb in firm contact with the thumb-mounting member. The thumb-mounting member is adjustable with respect to the hand-mounting member for comfort of the stroke victim.

(2) In a variant, the means for adjusting the length of either the first or second restraining straps is further comprised of a hooking element located adjacent to a first end of the restraining strap. A looping element extends from a second end of the restraining strap toward the first end whereby, when the hooking element is attached to the looping element at different points along the length of the restraining strap, the length of either of the first or the second restraining strap is adjusted.

(3) In another variant, the thumb-mounting member is lockable in a plurality of positions about a point where it is rotatably attached at its rear edge to the first side edge of the hand-mounting member.

(4) In yet another variant, a first accessory is provided. The first accessory is comprised of an armrest portion. The armrest portion is formed of planar semi-rigid resilient material, has a hand-shaped section and an extension section. The hand-shaped section has a distal end and a proximate end and is sized and shaped to support the antispasticity aid device. The extension section has a first end and a second end and has a length less than a distance from an armpit to a wrist of a stroke victim. The extension section is attached at the first end to the proximate end of the hand-shaped section. The first accessory is attached to the antispasticity aid device by either the first and the second fastening straps or the hooking and the looping fastening portions whereby when the first accessory is attached to the antispasticity aid device and the antispasticity aid device is attached to the hand of a stroke victim, an arm of the stroke victim may be comfortably positioned on an arm of an armchair or sofa.

(5) In yet a further variant, an upper padding portion is provided. The upper padding portion is formed of resilient padding material and is sized and shaped to fit over an upper surface of the extension section of the armrest portion. Whereby, when the first accessory is attached to the antispasticity aid device, the antispasticity aid device is attached to the hand of a stroke victim and the upper padding portion is positioned over the extension section, the arm of the stroke victim will be more comfortably positioned upon the first accessory.

(6) In still yet another variant, a lower padding portion is provided. The lower padding portion is formed of resilient padding material and is sized and shaped to fit over a lower surface of the extension section of the arm-rest portion. Whereby, when the first accessory is attached to the antispasticity aid device, the antispasticity aid device is attached to the hand of a stroke victim and the lower padding portion is positioned under the extension section, the arm of the stroke victim will be more comfortably positioned upon the first accessory.

(7) In a further variant, the extension section tapers in a vertical plane from the first end to the second end, thereby lowering a point of contact adjacent to an armpit of the stroke victim.

(8) In still another variant, the upper padding portion is formed of an FDA approved foam material.

(9) In yet another variant, the lower padding portion is formed of an FDA approved foam material.

(10) In still yet another variant, the extension section is covered with washable material.

(11) In yet another variant, the washable material is removable and replaceable.

(12) In a further variant, the second end of the extension section is comprised of a padded portion. The padded portion is sized and shaped to fit comfortably into the armpit of a stroke victim.

(13) In yet another variant, at least one pair of attachment slots is provided. The attachment slots are located along side edges of the extension section between the first end and the second end and is sized and shaped to accommodate an attachment strap.

(14) In another variant, either a hooking portion or a looping portion of a removable attachment device is provided. The portion is affixed to an upper surface of the hand shaped section. The portion provides a mechanism for removably attaching to the antispasticity aid device.

(15) In still yet another variant, a second accessory is provided. The second accessory is comprised of a support platform. The support platform is formed of planar semi-rigid, resilient material, an upper surface, a lower surface, has a hand-support section and an arm support section. The hand support section has a distal end and a proximate end and is sized and shaped to support the antispasticity aid device. The arm support section has a first end and a second end and has a length less than a distance from an armpit to a wrist of a stroke victim. The arm support section is attached at the first end to the proximate end of the hand-support section. The second accessory is attached to the antispasticity aid device using either the first and the second fastening straps or the hooking and the looping fastening portions. A planar base is provided. The planar base has an upper surface, a lower surface and is sized and shaped to fit beneath the support platform. A leaf spring is provided. The leaf spring has an upper section and a lower section and is formed with an acute angle between the upper section and the lower section. The upper section is affixed to the lower surface of the support platform and the lower section is affixed to the upper surface of the planar base. Whereby, when the second accessory is attached to the antispasticity aid device, and the antispasticity aid device is attached to the hand of a stroke victim, the second accessory will permit the stroke victim to apply force against the leaf spring to provide physical therapy for arm muscles of the stroke victim.

(16) In another variant, a padded material is provided. The padded material is affixed to the upper surface of the support platform.

(17) In yet another variant, a padded material is provided. The padded material is affixed to the lower surface of the support platform.

(18) In yet a further variant, a compression spring is provided. The compression spring is located between the upper surface of the planar base and an underside of the hand-support section of the support platform, thereby providing additional resistance to the stroke victim seeking physical therapy.

(19) In yet still another variant, at least one mounting bracket is provided. The mounting bracket is affixed to the lower surface of the planar hand-mounting member and is formed of resilient material. The mounting bracket is sized and shaped to removably attach to either a top bar of a walker or a cane handle whereby, the antispasticity aid device is easily attachable to either of the walker or cane handle by a stroke victim not able to adequately grip such devices with a hand.

(20) In a further variant, either a hooking portion or a looping portion of a removable attachment device is provided. The portion is affixed to the lower surface of the planar hand-mounting member. The portion provides a mechanism for removably attaching the antispasticity aid device to accessory devices.

(21) In still another variant, a third accessory is provided. The third accessory is comprised of an armrest portion. The armrest portion is formed of planar semi-rigid resilient material, has a hand-shaped section and an extension section. The hand-shaped section has an upper surface, a lower surface, a distal end and a proximate end and is sized and shaped to support the antispasticity aid device. The hand-shaped section has either a looping portion or a hooking portion of a removable attachment device affixed to the upper surface for attachment to the antispasticity aid device. The extension section has a first end and a second end and has a length greater than a distance from a back of a wrist of a stroke victim and is attached at the first end to the proximate end of the hand-shaped section. At least one reinforcing element is provided. The reinforcing element is formed of resilient material and is located within the armrest portion and extends from the second end of the extension section to at least into the hand shaped section. A mounting hinge is provided. The mounting hinge has a first portion and a second portion and is attached at the first portion to the reinforcing element adjacent to the second end of the extension section and is attached at the second portion to a wall adjacent to either a toilet or a bathtub. The mounting hinge maintains the third accessory in a position orthogonal to the wall whereby, when attached to the wall, the third accessory will provide a comfortable location for a stroke victim to rest an arm when using either the bathtub or the toilet.

(22) In still another variant, a fourth accessory is provided. The fourth accessory is comprised of a concave rest portion. The concave rest portion has an upper surface, a lower surface and is sized and shaped to accommodate an arm of a stroke victim using one of the antispasticity aid devices on the upper surface. A support portion is provided. The support portion has a top surface and a bottom surface. The support portion is of a length sufficient to support the rest portion and is attached at the top surface to the lower surface of the rest portion. The support portion is of a height sufficient to maintain the rest portion at a desired height. An attachment portion is provided. The attachment portion has an upper surface and a lower surface. The attachment portion is attached at the upper surface to the bottom surface of the support portion and is sized and shaped to fit frictionally over either the arm of a chair or sofa at the lower surface. Whereby, when fitted to either the arm of a chair or sofa, the fourth accessory will provide a comfortable and secure rest location for a stroke victim's arm.

(23) In yet another variant, a walker is provided. The walker has two pairs of downward pointing legs. Each of the pairs attaches at upper ends to a top cross bar. At least one leg of each pair is hingedly joined to at least one connecting bar. A support platform is provided. The support platform is pivotally attached to a bracket. The bracket is attached to the at least one connecting bar. The platform has a first end for supporting a wrist of a stroke victim and a second end for supporting the antispasticity aid device. The second end has either a hooking portion or a looping portion of a removable attachment device positioned upon an upper surface for removable attachment to the antispasticity aid device. At least one elastic member is provided. The elastic member is located between the bracket and an underside of the support platform. The elastic member provides resistive stability for the platform when supporting a hand and arm of a stroke victim.

(24) In yet a further variant, a fifth accessory is provided. The fifth accessory is comprised of a floor bracket. The floor bracket has an upper surface, a lower surface, a pivotal mounting bracket affixed to the upper surface and a non-slip finish on the lower surface. An adjustable support shaft is provided. The support shaft has an upper portion and a lower portion. The lower portion fits slidably within the upper portion and has a clamping mechanism for adjustably fastening the upper portion to the lower portion at a variety of heights. The lower portion has a fitting affixed at a lower end. The fitting is sized and shaped to fit the pivotal mounting bracket. The upper portion has a handle at an upper end. The handle is sized and shaped to accept the mounting bracket of the antispasticity aid device whereby, when the antispasticity aid device is removably affixed to the handle, a stroke victim will use the fifth accessory to exercise the arm and shoulder muscles.

(25) In still another variant, a sixth accessory is provided. The sixth accessory is comprised of a support tab. The support tab has a first surface, a second surface, an aperture penetrating the first and second surfaces and either a hooking portion or a looping portion of a removable attachment device affixed to one of the first or second surfaces. The portion provides a mechanism for removably attaching the support tab to the antispasticity aid device. An elastic chord is provided. The elastic chord has a first end, a second end and is attached at the first end to the support tab through the aperture. The elastic chord has a mechanism at the second end for forming a loop adjacent to the second end. The loop serves to attach the elastic chord to a support fixture whereby, when the antispasticity aid device is attached to the hand of a stroke victim, the antispasticity aid device is attached to the support tab and the loop is attached to the fixture, the hand and arm of the stroke victim will be suspended for ease of washing.

(26) In yet another variant, the sixth accessory is comprised of a weakened portion in the elastic chord. The weakened portion provides a safety feature for a stroke victim in the event the stroke victim should fall. The safety feature prevents the stroke victim from being suspended by the sixth accessory.

(27) In still a further variant, a coupling in the elastic chord is provided. The coupling has an attaching portion and a receiving portion. The attaching portion is affixed to an upper end of a lower portion of the elastic chord and has a head section and a reduced cross-section neck section located below the head section. The receiving portion is affixed to a lower end of an upper portion of the elastic chord having a cavity. The cavity is sized and shaped to frictionally fit over the attaching portion and has a resilient surrounding lower rim. The rim is sized and shaped to fit into the neck section whereby, when a downward pressure on the sixth accessory exceeds pressure required to locate the attaching portion in the receiving portion, the attaching portion and the receiving portions will separate. This provides a safety feature for a stroke victim using the sixth accessory.

(28) In yet a further variant, a seventh accessory is provided. The seventh accessory is comprised of a resilient arm support member. The arm support member has a first end, a second end and is formed into a loop. The loop is joined by an intermediate bridging member. The resilient arm member is sized and shaped to fit frictionally over a wheelchair arm and to provide a channel at an upper surface suitable for resting of a stroke victim's arm. At least one retaining strap is provided. The retaining strap has a first portion and a second portion. Each of the portions are attached to an outer edge of the loop and has either a looping means or a hooking means attached to the portions to permit the retaining strap to be fastened over an arm of a stroke victim.

(29) In still a further variant, a hand support platform is provided. The hand support platform is attached to at least one end of the loop and is sized and shaped to fit beneath the antispasticity aid device. The hand support platform has a series of slots for accepting retaining straps to hold the antispasticity aid device to the hand support platform.

(30) In another variant, an eighth accessory is provided. The eighth accessory is comprised of a vertically oriented mounting structure. The mounting structure has an upper end, a lower end, a support base located at the lower end and a central adjusting tract. A bearing mount is provided. The bearing mount is slidably affixed to the central adjusting track and has a curved exterior edge. A bearing is provided. The bearing is affixed to a center of the bearing mount. A planar positioning member is provided. The positioning member has a perimeter, a front surface, a rear surface and is affixed to the bearing at a center portion of the rear surface. A planar, L-shaped control bracket is provided. The control bracket is pivotally mounted adjacent to a corner of the L-shape to the front surface of the positioning member adjacent to the perimeter. The control bracket has a control bracket bearing mounted at one end of the L-shape. At least one stop pin is provided. The stop pin is mounted to the front surface of the positioning member and is located between arms of the L-shaped control bracket. An antispasticity aid support member is provided. The support member has an upper surface and a lower surface. The support member is pivotally mounted to the control bracket bearing and is sized and shaped to support the antispasticity aid device. The support member has either a hooking portion or a looping portion of a removable attachment device affixed to the upper surface of the support member for attachment to the antispasticity aid device. A first elastic member is provided. The first elastic member has a first end and a second end. The first elastic member is attached at the first end to the rear surface of the planar positioning member adjacent to the perimeter and is attached at the second end to the curved exterior edge of the bearing mount whereby, when the antispasticity aid device is attached to a hand of a stroke victim and the antispasticity aid device is attached to the support member, the eighth accessory will provide a mechanism for exercising arm muscles of the stroke victim, permitting rising extension of the arm muscles.

(31) In yet another variant, a second elastic member is provided. The elastic member has a first end and a second end. The elastic member is attached at the first end to the front surface of the planar positioning member inward from the perimeter and is attached at the second end to the support member. This provides additional stability for the arm of the stroke victim as the eighth accessory is used for exercising the arm of the stroke victim.

(32) In still a further variant, a ninth accessory is provided. The ninth accessory has a support platform. The support platform is formed of planar semi-rigid, resilient material and has a hand-support section and an arm support section and is attached to a wheelchair. The hand-support section has a distal end and a proximate end and is sized and shaped to support the antispasticity aid device. The arm support section has a first section and a second section. The first section has a first end and a second end. The second section has a first end and a second end. The first section of the arm support section is attached at the first end to the proximate end of the hand-support section. An elastic element is provided. The elastic element has a front end and a rearward end. The front end of the elastic element is attached to the second end of the first section of the arm support section and the rearward end of the elastic element is attached to the first end of the second section of the arm support section. Whereby, when the ninth accessory is attached to the antispasticity aid device and the antispasticity aid device is attached to the hand of a stroke victim, the ninth accessory will permit the stroke victim to apply force against the elastic element to provide physical therapy for arm muscles of the stroke victim.

(33) In another variant, a means for attaching the front end of the elastic element to the second end of the first section of the arm support section and the rearward end of the elastic element to the first end of the second section of the arm support section is provided.

(34) In still another variant, at least one bracket is provided. The bracket has a first end, a second end and is attached to either the second end of the first section of the arm support section or the first end of the second section of the arm support section to the first end of the bracket.

(35) In a further variant, an extension spring is provided. The extension spring has a front end and a rearward end. The front end of the extension spring is attached to the second end of the first section of the arm support section and the rearward end of the extension spring is attached to the first end of the second section of the arm support section.

(36) In yet another variant, a mechanism of attaching the support platform at the second end of the second section of the arm support section to a hollow tube at the rear of the wheelchair is provided.

(37) In still a further variant, a plurality of detents is provided. The detents are located at the rear edge of the thumb-mounting member. A ball channel is provided. The ball channel is located in either the first side edge or the second side edge of the hand-mounting member. The ball channel has a compression spring located within the channel. A positioning ball is provided. The ball is sized and shaped to fit slidably within the channel and to fit within the detents. The ball is maintained in one of the detents by the compression spring whereby, when pressure is applied to a side edge of the thumb-mounting member, the ball will be moved from one detent to the next. The compression spring tends to maintain a position of the thumb-mounting member with respect to the hand-mounting member.

(38) In yet another variant, a plurality of notches is provided. The notches are located at either the first side edge or the second side edge of the hand-mounting member. A protruding finger is provided. The protruding finger is located at the rear edge of the thumb-mounting member and is sized and shaped to removably engage any one of the notches whereby, when the protruding finger is located in one of the notches, the finger will maintain a position of the thumb-mounting member with respect to the hand-mounting member.

(39) In still another variant, a raised padding portion is provided. The raised padding portion is formed of resilient padding material and is sized and shaped to fit over an upper surface of the planar hand-mounting member. Whereby, when the raised padding portion is fit over the upper surface of the planar hand-mounting member and the raised padding portion is attached to a hand of a stroke victim, the knuckles of the stroke victim will be elevated above the fingertips of the stroke victim thereby allowing the hand of the stroke victim to be comfortably positioned on the planar hand-mounting member.

(40) In yet still a further variant, the raised padding portion is formed of an FDA approved foam material.

(41) In still a further variant, the planar hand-mounting member is covered with a washable material.

(42) In a final variant, the washable material is removable and replaceable.

DESCRIPTION OF THE DRAWINGS

FIG. 6 is a side elevational view of a second accessory illustrating the support platform and the planar base;

FIG. 7 is a side elevational view of the second accessory illustrating the compression spring located between the planar base and the support platform;

FIG. 8 is a perspective view of the second accessory illustrating the stroke victim seeking physical therapy provided by the additional resistance of the compression spring;

FIG. 15 is a perspective view of a fifth accessory illustrating the floor bracket, the adjustable support shaft, the lower portion and the upper portion with a handle;

FIG. 16 is a perspective view of the sixth accessory illustrating the support tab, the elastic cord and the weakened portion in the elastic cord;

FIG. 17 is a detailed side elevational view of the coupling in the elastic cord illustrating the attaching portion and the receiving portion;

FIG. 18 is a perspective view of the seventh accessory illustrating the resilient arm support member, the intermediate bridging member and the retaining strap;

FIG. 18A is a perspective view of the seventh accessory fit frictionally over a wheelchair arm and providing a channel at the upper surface for resting a stroke victim's arm;

FIG. 19 is a perspective view of the hand support platform attached to at least one end of the loop;

DETAILED DESCRIPTION OF THE PREFERRED EMBODIMENT

The present invention addresses all of the deficiencies or prior stroke victim aid inventions and satisfies all of the objectives described above.

Figure 1:
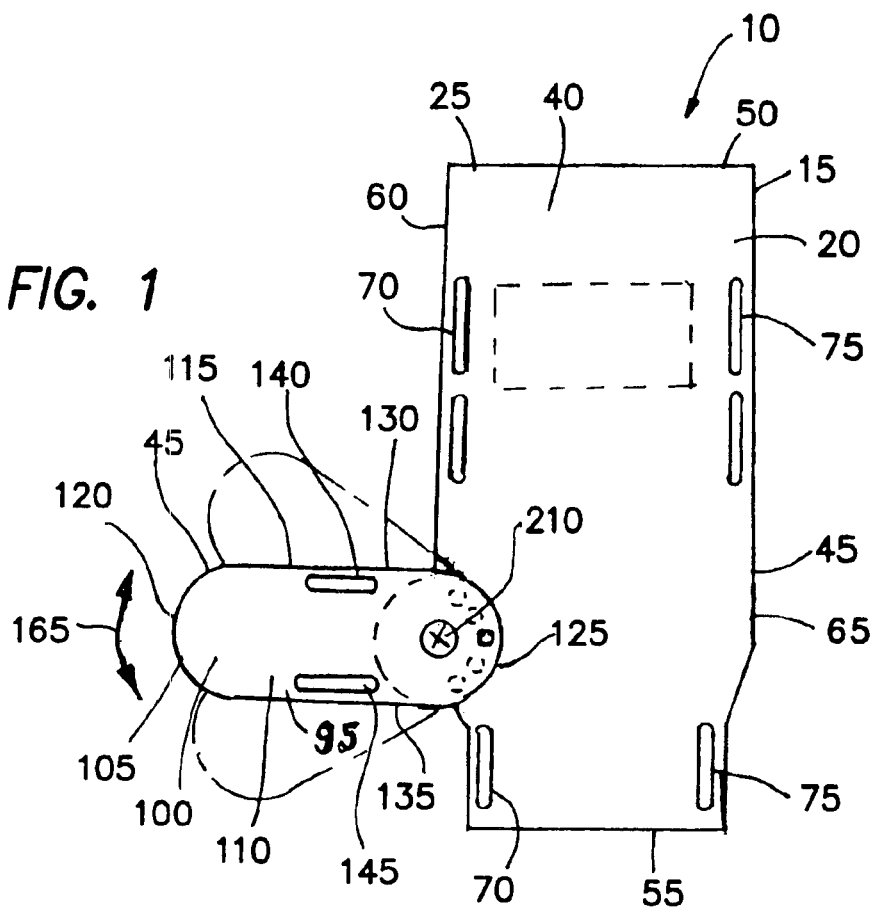
FIG. 1 is a plan view of the preferred embodiment of the invention including the rotatably attached thumb-mounting member.
Figure 2:
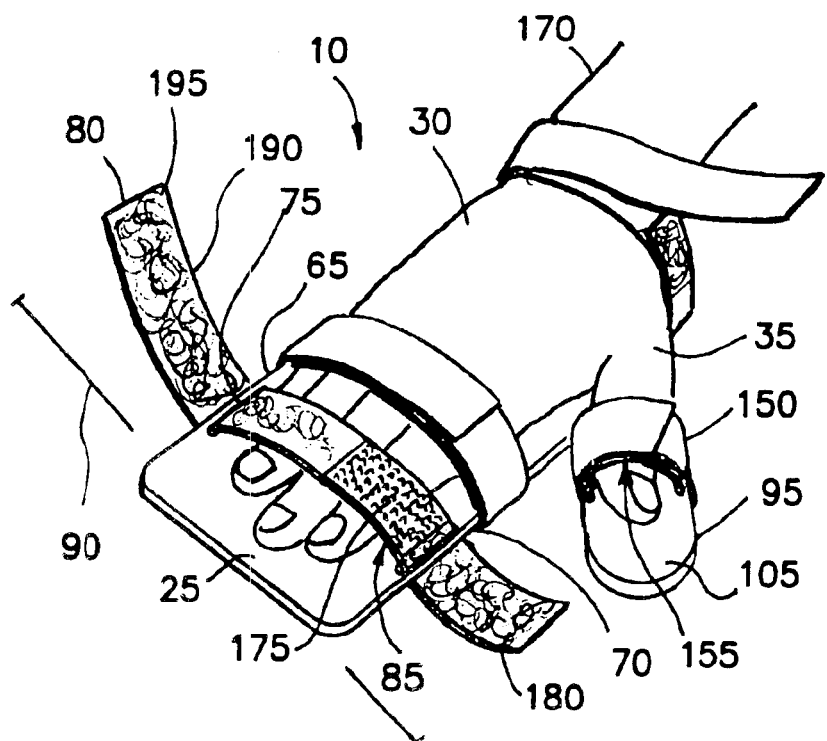
FIG. 2 is a perspective view of the FIG. 1 embodiment illustrating the first and second restraining straps.
Figure 3:
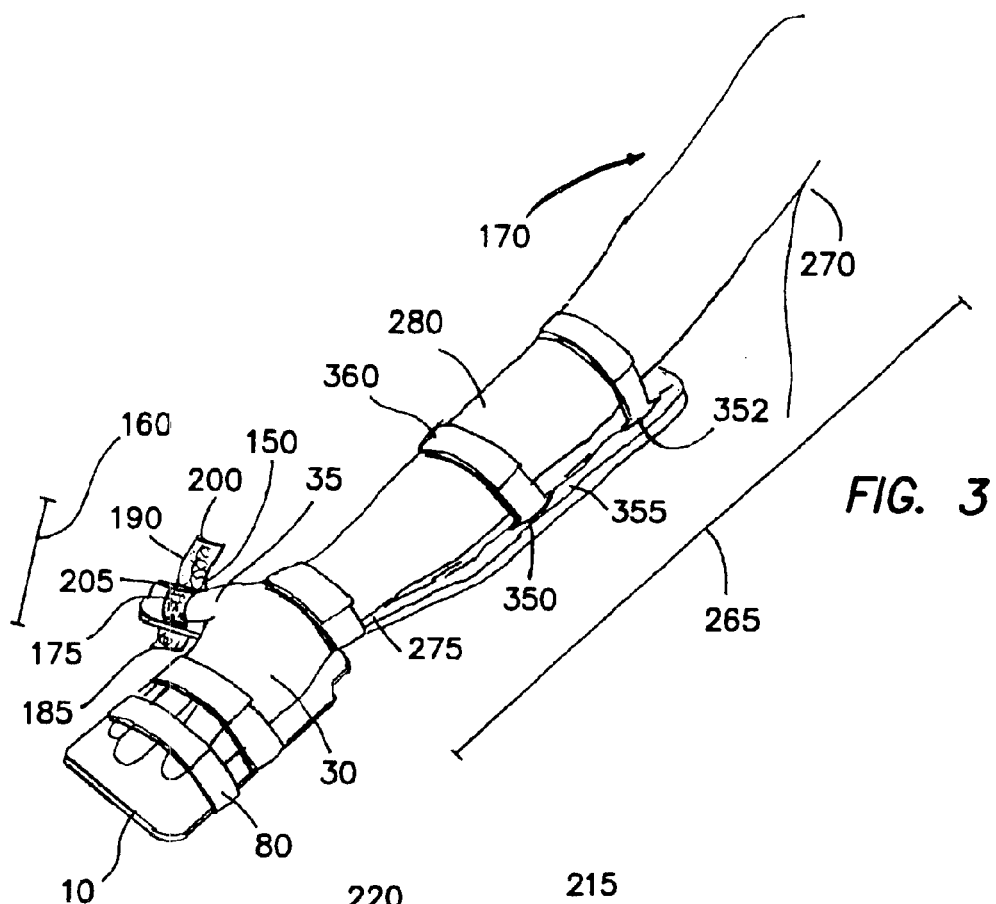
FIG. 3 is a perspective view of the FIG. 1 embodiment illustrating the first accessory comprised of an armrest portion.

(1) As shown in FIGS. 1–3, an antispasticity aid device 10 providing the desired features may be constructed from the following components. A planar hand-mounting member 15 is provided. The planar hand-mounting member 15 is formed of rigid material 20 and is sized and shaped to extend beyond the outer dimensions 25 of a human hand 30 without a thumb 35. The planar hand-mounting member 15 has an upper surface 40, a lower surface 45, a front edge 50, a rear edge 55, a first side edge 60 and a second side edge 65. The hand-mounting member 15 has at least two first fastening slots 70, 75 located adjacent to the first 60 and second 65 side edges, respectively. A first restraining strap 80 is provided. The first restraining strap 80 is size and shaped to fit slidably through the first fastening slots 70, 75 and has a means 85 for adjusting a length 90 of the first strap 80.

A thumb-mounting member 95 is provided. The thumb-mounting member 95 is formed of rigid material 100 and is sized and shaped to extend beyond the outer dimensions 105 of the human thumb 35. The thumb-mounting member 95 has an upper surface 110, a lower surface 115, a front edge 120, a rear edge 125, a first side edge 130 and a second side edge 135. The thumb-mounting member 95 has at least two second fastening slots 140, 145 located adjacent to the first 130 and the second 135 side edges of the thumb-mounting member 95, respectively. A second restraining strap 150 is provided. The second strap 150 is sized and shaped to fit slidably through the second fastening slots 140, 145 and has a means 155 for adjusting a length 160 of the second strap 150. The thumb-mounting member 95 is rotatably attached at its rear edge 125 to the first side edge 60 of the hand-mounting member 15. This permits the thumb-mounting member 95 to rotate through an arc 165 in the plane of the hand-mounting member 95 whereby, when the hand 30 of a stroke victim 170 is placed upon the hand-mounting member 15, the first restraining strap 80 is located over the hand 30 and through the first fastening slots 70, 75.

The length 90 of the first restraining strap 80 is adjusted to hold the hand 30 in firm contact with the hand-mounting member 15 and when the thumb 35 of a stroke victim 170 is placed upon the thumb-mounting member 95, the second restraining strap 150 is located over the thumb 35 and through the second fastening slots 140, 145. The length 160 of the second restraining strap 150 is adjusted to hold the thumb 35 in firm contact with the thumb-mounting member 95. The thumb-mounting member 95 is adjustable with respect to the hand-mounting member 15 for comfort of the spasticity victim 170.

(2) In a variant, as shown in FIG. 2 and FIG. 3, the means 85, 155 for adjusting the length 90, 160 of either the first 80 or second 150 restraining straps is further comprised of a hooking element 175 located adjacent to a first end 180, 185 of the restraining strap 80, 150. A looping element 190 extends from a second end 195, 200 of the restraining strap 80, 150 toward the first end 180, 185 whereby, when the hooking element 175 is attached to the looping element 190 at different points along the length 90, 160 of the restraining strap 80, 150, the length 90, 160 of either of the first 80 or the second 150 restraining strap is adjusted.

(3) In another variant, as shown in FIG. 1, the thumb-mounting member 95 is lockable in a plurality of positions about a point 210 where it is rotatably attached at its rear edge 125 to the first side edge 60 of the hand-mounting member 15.

(4) In yet another variant, as shown in FIGS. 3–5, 5A and 5B, a first accessory 215 is provided. The first accessory 215 is comprised of an armrest portion 220. The armrest portion 220 is formed of planar semi-rigid resilient material 225, has a hand-shaped section 230 and an extension section 235. The hand-shaped section 230 has a distal end 240 and a proximate end 245 and is sized and shaped to support the antispasticity aid device 10. The extension section 235 has a first end 250 and a second end 255 and has a length 260 less than a distance 265 from an armpit 270 to a wrist 275 of a stroke victim 170. The extension section 235 is attached at the first end 250 to the proximate end 245 of the hand-shaped section 230. The first accessory 215 is attached to the antispasticity aid device 10 by either the first 80 and the second 150 fastening straps or the hooking 175 and the looping 190 fastening portions whereby when the first accessory 215 is attached to the antispasticity aid device 10 and the antispasticity aid device 10 is attached to the hand 30 of a stroke victim 170, an arm 280 of the stroke victim 170 may be comfortably positioned on an arm 285 of an armchair 290 or sofa (not shown).

Figure 5:
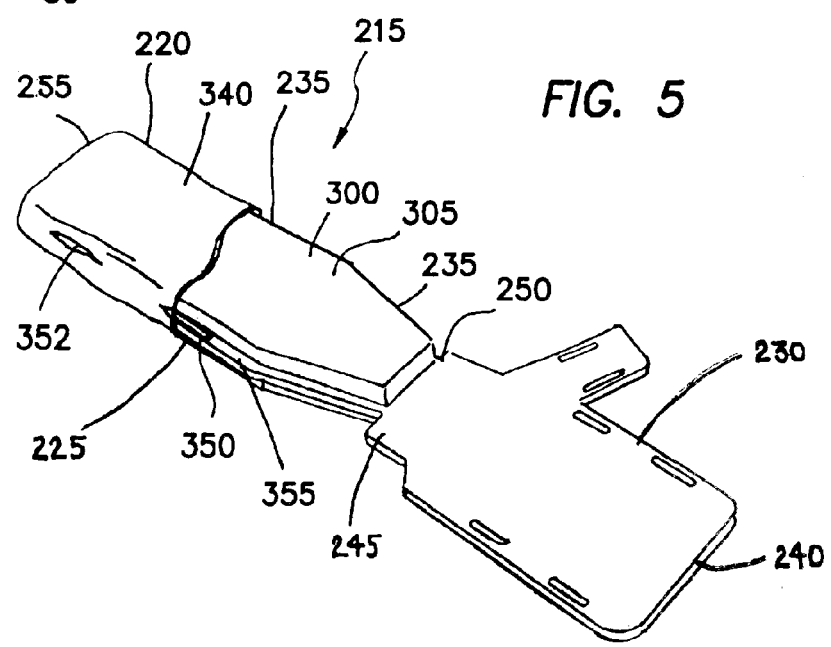
FIG. 5 is a perspective view of the first accessory illustrating the washable material covering the extension section.
Figure 4:
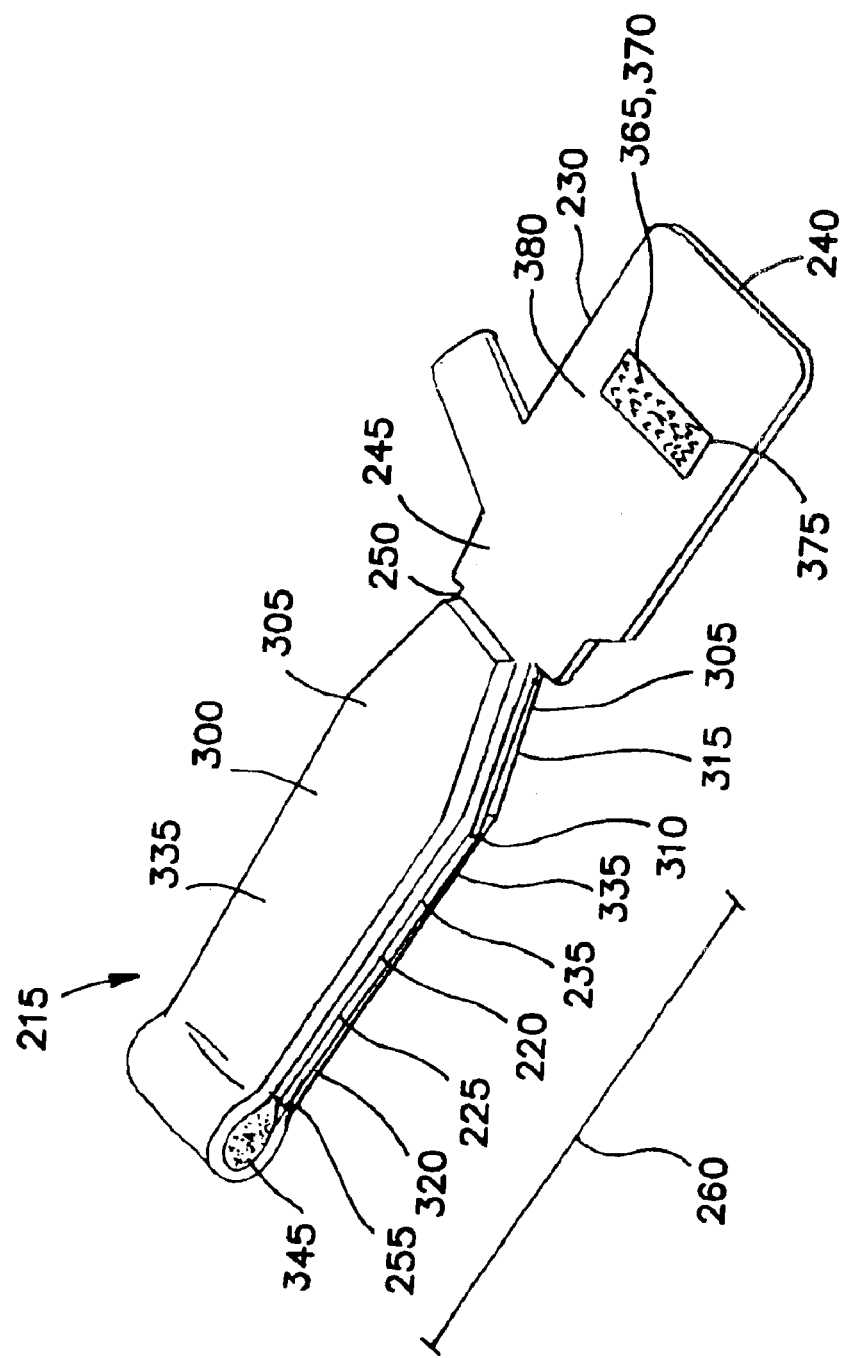
FIG. 4 is a perspective view of a first accessory illustrating the upper and lower padding portions and the padded portion on the second end of the extension section.

(5) In yet a further variant, as shown in FIG. 4 and FIG. 5, an upper padding portion 300 is provided. The upper padding portion 300 is formed of resilient padding material 305 and is sized and shaped to fit over an upper surface 310 of the extension section 235 of the arm-rest portion 220. Whereby, when the first accessory 215 is attached to the antispasticity aid device 10, the antispasticity aid device 10 is attached to the hand 30 of a stroke victim 170 and the upper padding portion 300 is positioned over the extension section 235, the arm 280 of the stroke victim 170 will be more comfortably positioned upon the first accessory 215.

(6) In still yet another variant, as shown in FIG. 4 and FIG. 5, a lower padding portion 315 is provided. The lower padding portion 315 is formed of resilient padding material 305 and is sized and shaped to fit over a lower surface 320 of the extension section 235 of the arm-rest portion 220. Whereby, when the first accessory 215 is attached to the antispasticity aid device 10, the antispasticity aid device 10 is attached to the hand 30 of a stroke victim 170 and the lower padding portion 315 is positioned under the extension section 235, the arm 280 of the stroke victim 170 will be more comfortably positioned upon the first accessory 215.

Figure 4A:
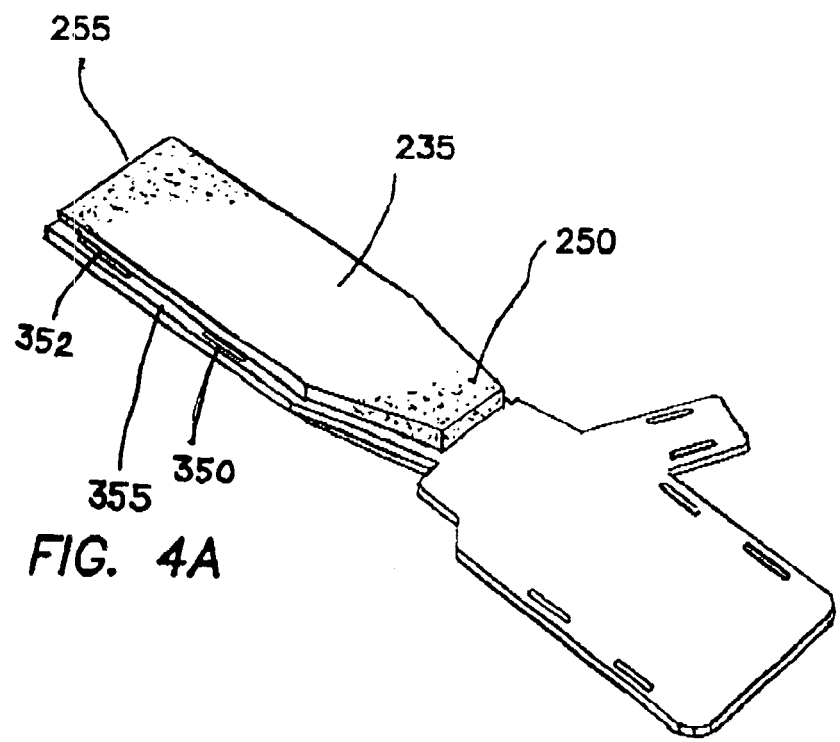
Figure 4B:
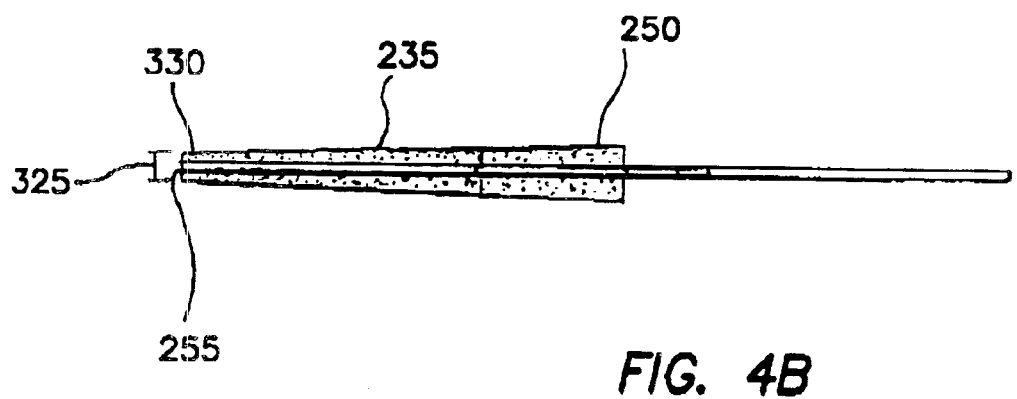
Figure 5A:
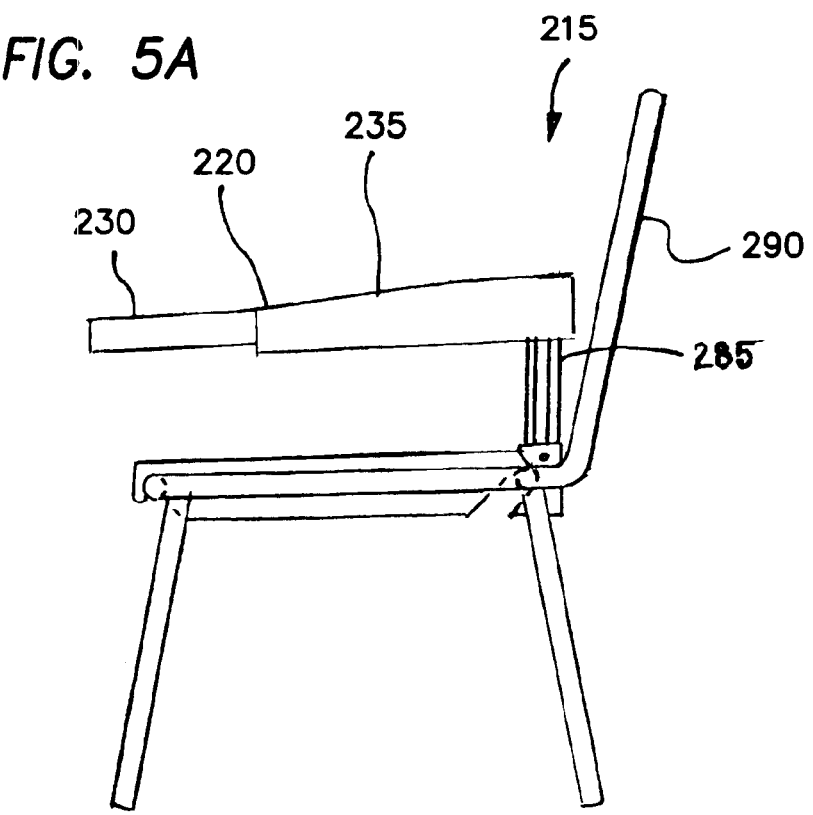
FIG. 5A is a side elevational view of the first accessory positioned on an arm of an armchair.
Figure 5B:
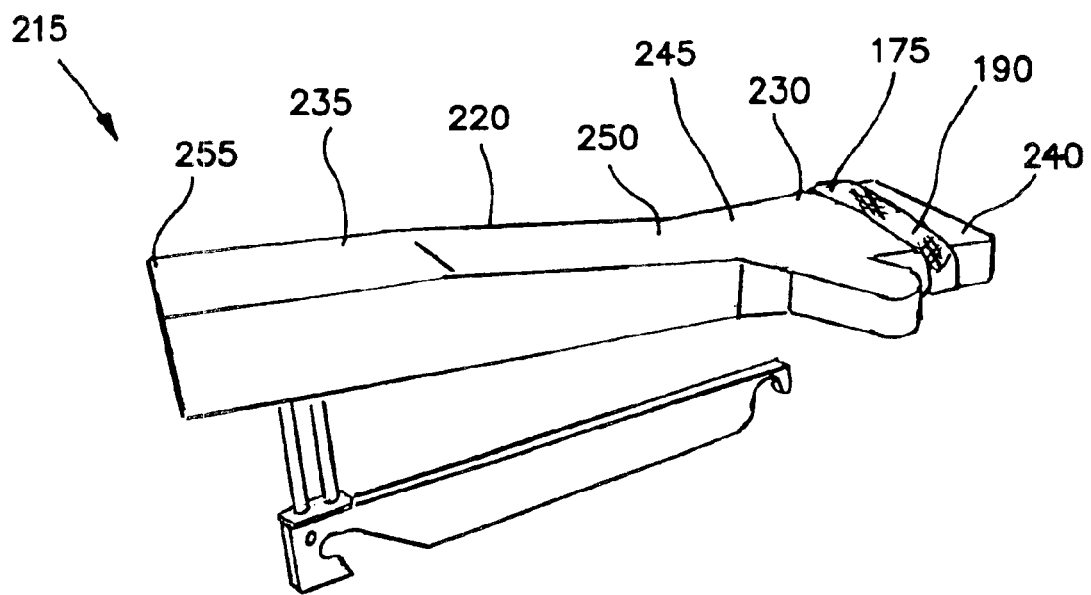
FIG. 5B is a perspective view of the first accessory illustrating the hand-shaped section, the extension section and the upper and lower padding portion.

(7) In a further variant, as shown in FIG. 4A and FIG. 4B, the extension section 235 tapers in a vertical plane 325 from the first end 250 to the second end 255, thereby lowering a point of contact 330 adjacent to the armpit 270 of the stroke victim 170.

(8) In still another variant, as shown in FIG. 4 and FIG. 5, the upper padding portion 300 is formed of an FDA approved foam material 335.

(9) In yet another variant, as shown in FIG. 4 and FIG. 5, the lower padding portion 315 is formed of an FDA approved foam material 335.

(10) In still yet another variant, as shown in FIG. 5, the extension section 235 is covered with washable material 340.

(11) In yet another variant, as shown in FIG. 5, the washable material 340 is removable and replaceable.

(12) In a further variant, as shown in FIG. 4, the second end 255 of the extension section 235 is comprised of a padded portion 345. The padded portion 345 is sized and shaped to fit comfortably into the armpit 270 of a stroke victim 170.

(13) In yet another variant, as shown in FIG. 3, FIG. 4A and FIG. 5, at least one pair of attachment slots 350, 352 is provided. The attachment slots 350, 352 are located along side edges 355 of the extension section 235 between the first end 250 and the second end 255 and is sized and shaped to accommodate an attachment strap 360.

(14) In another variant, as shown in FIG. 4, either a hooking portion 365 or a looping portion 370 of a removable attachment device 375 is provided. The portion 365, 370 is affixed to an upper surface 380 of the hand shaped section 230. The portion 365, 370 provides a mechanism for removably attaching to the antispasticity aid device 10.

(15) In still yet another variant, as shown in FIG. 6, a second accessory 385 is provided. The second accessory 385 is comprised of a support platform 390. The support platform 390 is formed of planar semi-rigid, resilient material 225, has an upper surface 391, a lower surface 392, has a hand-support section 395 and an arm support section 400. The hand support section 395 has a distal end 405, a proximate end 410 and is sized and shaped to support the antispasticity aid device 10. The arm support section 400 has a first end 415, a second end 420 and has a length 425 less than a distance 265 from an armpit 270 to a wrist 275 of a stroke victim 170. The arm support section 400 is attached at the first end 415 to the proximate end 410 of the hand-support section 395. The second accessory 385 is attached to the antispasticity aid device 10 using either the first 80 and the second 150 fastening straps or the hooking 175 and the looping 190 fastening portions. A planar base 420 is provided. The planar base 420 has an upper surface 421, a lower surface 422 and is sized and shaped to fit beneath the support platform 390. A leaf spring 425 is provided. The leaf spring 425 has an upper section 430 and a lower section 435 and is formed with an acute angle 440 between the upper section 430 and the lower section 435. The upper section 430 is affixed to the lower surface 392 of the support platform 390 and the lower section 435 is affixed to the upper surface 421 of the planar base 420. Whereby, when the second accessory 385 is attached to the antispasticity aid device 10, and the antispasticity aid device 10 is attached to the hand 30 of a stroke victim 170, the second accessory 385 will permit the stroke victim 170 to apply force against the leaf spring 425 to provide physical therapy for arm muscles 440 of the stroke victim 170.

(16) In another variant, as shown in FIGS. 6–8, a padded material 445 is provided. The padded material 445 is affixed to the upper surface 391 of the support platform 390.

(17) In another variant, as shown in FIGS. 6–8, a padded material 445 is provided. The padded material 445 is affixed to the lower surface 392 of the support platform 390.

(18) In yet a further variant, as shown in FIG. 7 and FIG. 8, a compression spring 455 is provided. The compression spring 455 is located between the upper surface 421 of the planar base 420 and an underside 460 of the hand-support section 395 of the support platform 390, thereby providing additional resistance to the stroke victim 170 seeking physical therapy.

Figure 9:
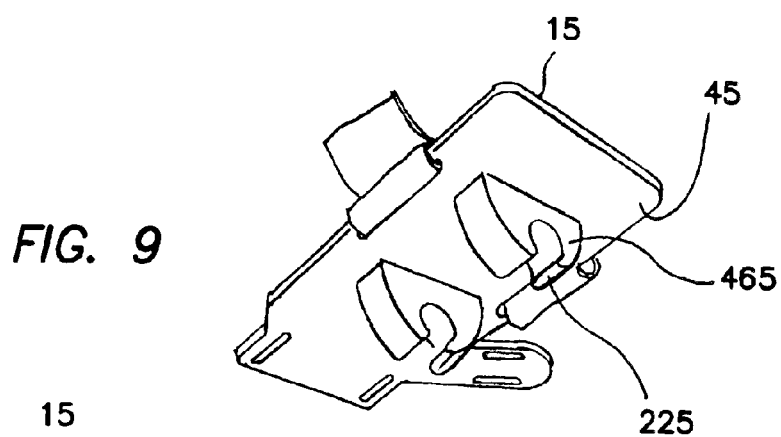
FIG. 9 is a perspective view of the underside of the mounting bracket affixed to the lower surface of the planar hand-mounting member.
Figures 13, 14:
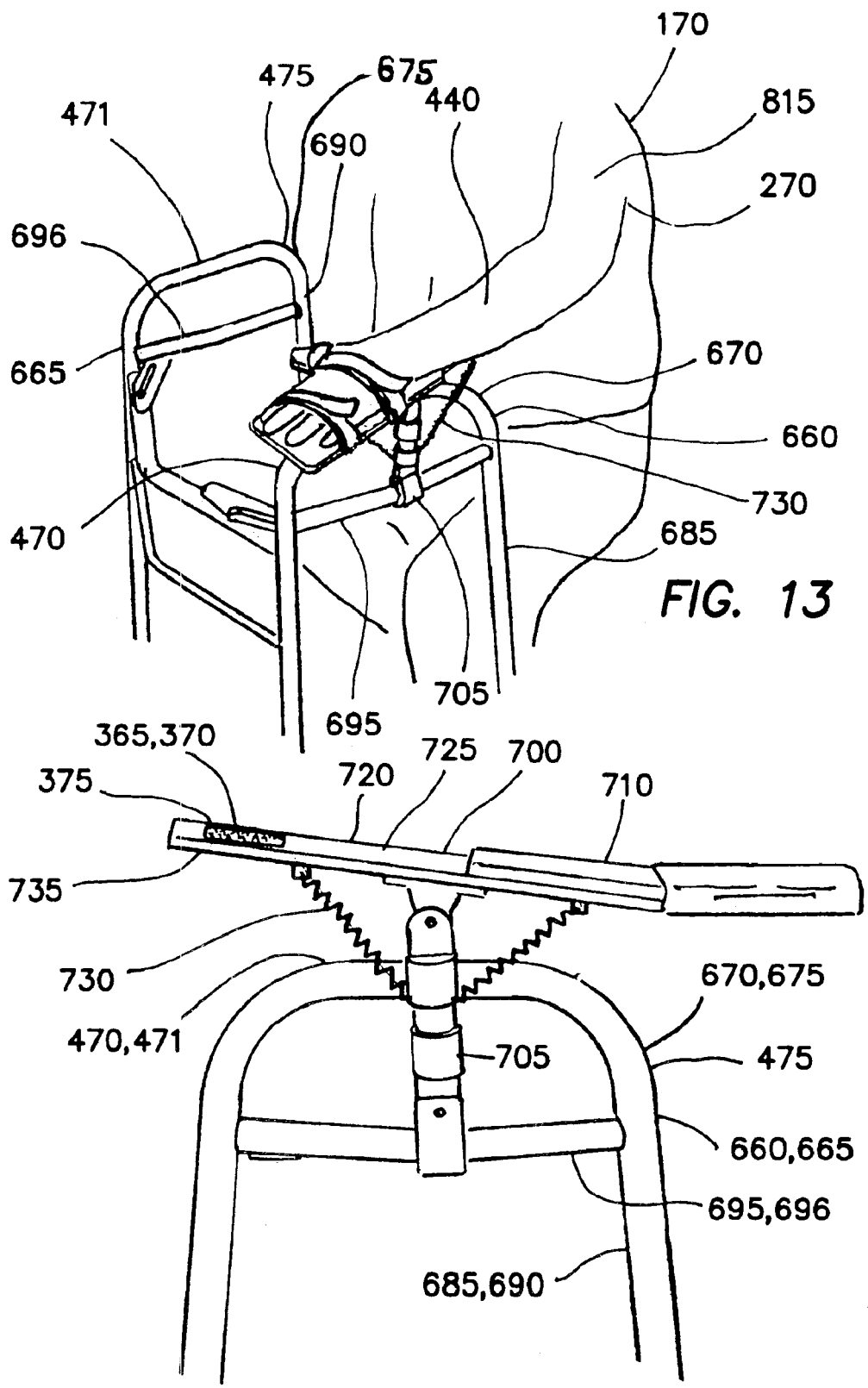
FIG. 13 is perspective view of the support platform pivotally attached to a bracket attached to the connecting bar of a walker.
FIG. 14 is an elevated plan view of the support platform illustrating the at least one elastic member located between the bracket and the support platform.

(19) In yet still another variant, as shown in FIG. 9, FIG. 13 and FIG. 15, at least one mounting bracket 465 is provided. The mounting bracket 465 is affixed to the lower surface 45 of the planar hand-mounting member 15 and is formed of resilient material 225. The mounting bracket 465 is sized and shaped to removably attach to either a top bar 470 of a walker 475 or a cane handle 480 whereby, the antispasticity aid device 10 is easily attachable to either of the walker 475 or cane handle 480 by a stroke victim 170 not able to adequately grip such devices 475, 480 with a hand 30.

Figure 10:
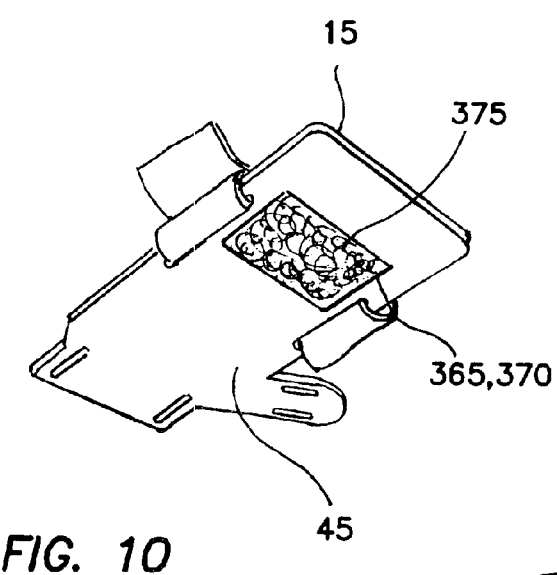
FIG. 10 is a perspective view of the underside of the hooking or looping portion of a removable attachment device affixed to the lower surface of the planar hand-mounting member.

(20) In a further variant, as shown in FIG. 10, either a hooking portion 365 or a looping portion 370 of a removable attachment device 375 is provided. The portion 365, 370 is affixed to the lower surface 45 of the planar hand-mounting member 15. The portion 365, 370 provides a mechanism for removably attaching the antispasticity aid device 10 to accessory devices 215, 385, 485, 585, 740, 820, 935, 1020, 1195.

Figures 11, 12:
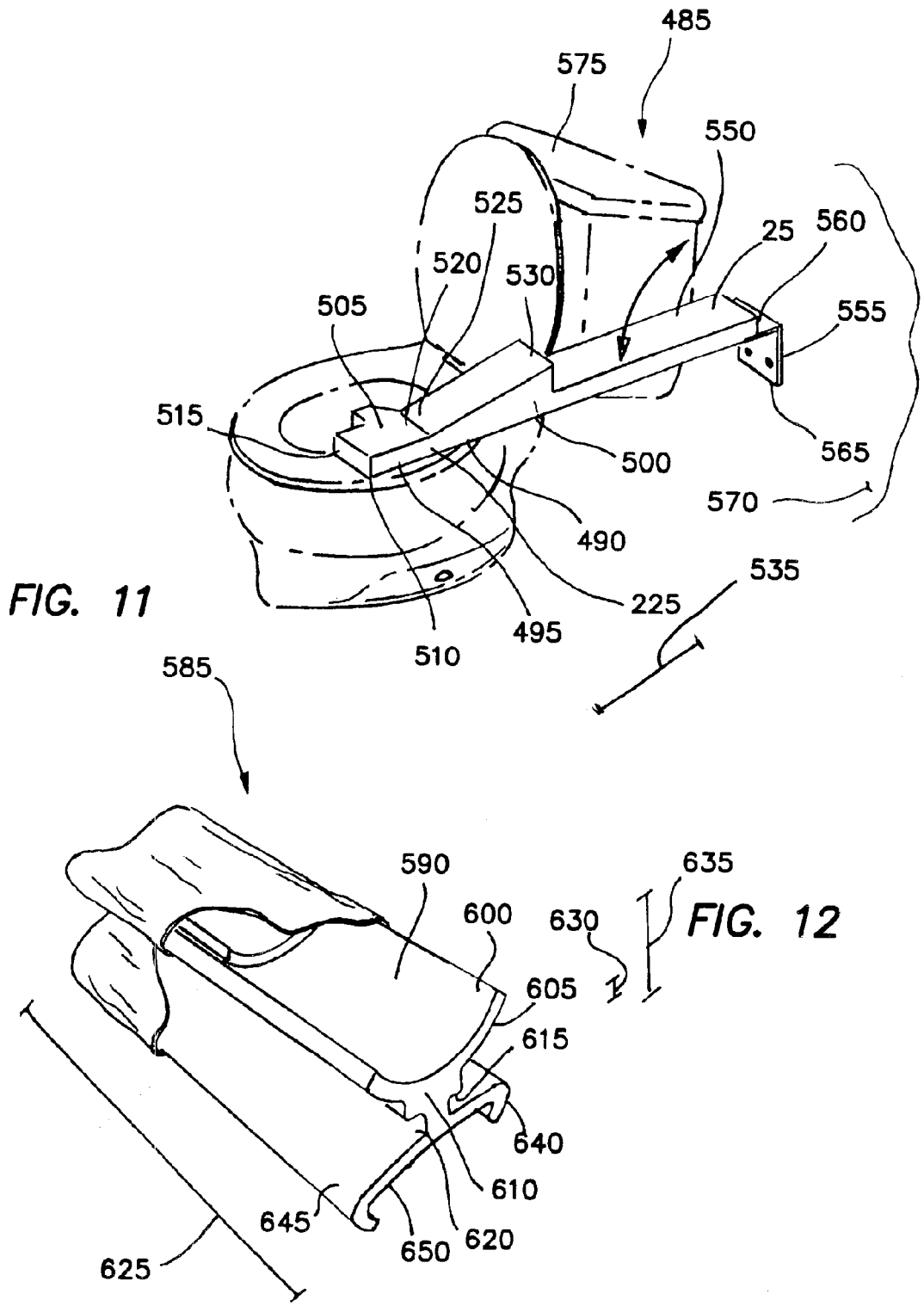
FIG. 11 is a perspective view of a third accessory illustrating the arm-rest portion, the hand-shaped section, the extension section and the mounting hinge.
FIG. 12 is a perspective view of a fourth accessory illustrating the concave rest portion, the support portion and the attachment portion.

(21) In another variant, as shown in FIG. 11, a third accessory 485 is provided. The third accessory 485 is comprised of an arm-rest portion 490. The arm-rest portion 490 is formed of planar semi-rigid resilient material 225, has a hand-shaped section 495 and an extension section 500. The hand-shaped section 495 has an upper surface 505, a lower surface 510, a distal end 515 and a proximate end 520 and is sized and shaped to support the antispasticity aid device 10. The hand-shaped section 495 has either a looping portion 370 or a hooking portion 365 of a removable attachment device 375 affixed to the upper surface 505 for attachment to the antispasticity aid device 10. The extension section 500 has a first end 525 and a second end 530 and has a length 535 greater than a distance from a back of a wrist 275 of a stroke victim 170 and is attached at the first end 525 to the proximate end 520 of the hand-shaped section 495. At least one reinforcing element 550 is provided. The reinforcing element 550 is formed of resilient material 25 and is located within the arm-rest portion 490 and extends from the second end 530 of the extension section 500 to at least into the hand shaped section 495. A mounting hinge 555 is provided. The mounting hinge 555 has a first portion 560 and a second portion 565 and is attached at the first portion 560 to the reinforcing element 550 adjacent to the second end 530 of the extension section 500 and is attached at the second portion 565 to a wall 570 adjacent to either a toilet 575 or a bathtub (not shown). The mounting hinge 555 maintains the third accessory 485 in a position orthogonal to the wall 570 whereby, when attached to the wall 570, the third accessory 485 will provide a comfortable location for a stroke victim 170 to rest an arm 280 when using either the bathtub (not shown) or the toilet 575.

(22) In still another variant, as shown in FIG. 12, a fourth accessory 585 is provided. The fourth accessory 585 is comprised of a concave rest portion 590. The concave rest portion 590 has an upper surface 600, a lower surface 605 and is sized and shaped to accommodate an arm 280 of a stroke victim 170 using one of the antispasticity aid devices 10 on the upper surface 600. A support portion 610 is provided. The support portion 610 has a top surface 615 and a bottom surface 620. The support portion 610 is of a length 625 sufficient to support the rest portion 590 and is attached at the top surface 615 to the lower surface 605 of the rest portion 590. The support portion 610 is of a height 630 sufficient to maintain the rest portion 590 at a desired height 635. An attachment portion 640 is provided. The attachment portion 640 has an upper surface 645 and a lower surface 650. The attachment portion 640 is attached at the upper surface 645 to the bottom surface 620 of the support portion 610 and is sized and shaped to fit frictionally over either the arm 285 of a chair 290 or sofa (not shown) at the lower surface 650. Whereby, when fitted to either the arm 285 of a chair 290 or sofa (not shown), the fourth accessory 585 will provide a comfortable and secure rest location for a stroke victim's arm 280.

(23) In yet another variant, as shown in FIG. 13 and FIG. 14, a walker 475 is provided. The walker 475 has two pairs of downward pointing legs 660, 665. Each of the pairs 660, 665 attaches at upper ends 670, 675 to a top cross bar 470, 471. At least one leg 685, 690 of each pair 660, 665 is hingedly joined to at least one connecting bar 695, 696. A support platform 700 is provided. The support platform 700 is pivotally attached to a bracket 705. The bracket 705 is attached to the at least one connecting bar 695, 696. The platform 700 has a first end 710 for supporting a wrist 275 of a stroke victim 170 and a second end 720 for supporting the antispasticity aid device 10. The second end 720 has either a hooking portion 365 or a looping portion 370 of a removable attachment device 375 positioned upon an upper surface 725 for removable attachment to the antispasticity aid device 10. At least one elastic member 730 is provided. The elastic member 730 is located between the bracket 705 and an underside 735 of the support platform 700. The elastic member 730 provides resistive stability for the platform 700 when supporting the hand 30 and arm 280 of a stroke victim 170.

(24) In yet a further variant, as shown in FIG. 9 and FIG. 15, a fifth accessory 740 is provided. The fifth accessory 740 is comprised of a floor bracket 745. The floor bracket 745 has an upper surface 750, a lower surface 755, a pivotal mounting bracket 760 affixed to the upper surface 750 and a non-slip finish 765 on the lower surface 755. An adjustable support shaft 770 is provided. The support shaft 770 has an upper portion 775 and a lower portion 780. The lower portion 780 fits slidably within the upper portion 775 and has a clamping mechanism 785 for adjustably fastening the upper portion 775 to the lower portion 780 at a variety of heights. The lower portion 780 has a fitting 795 affixed at a lower end 800. The fitting 795 is sized and shaped to fit the pivotal mounting bracket 760. The upper portion 775 has a handle 480 at an upper end 810. The handle 480 is sized and shaped to accept the mounting bracket 465 of the antispasticity aid device 10 whereby, when the antispasticity aid device 10 is removably affixed to the handle 480, a stroke victim 170 will use the fifth accessory 740 to exercise the arm 440 and shoulder 815 muscles.

(25) In still another variant, as shown in FIG. 16, a sixth accessory 820 is provided. The sixth accessory 820 is comprised of a support tab 825. The support tab 825 has a first surface 830, a second surface 835, an aperture 840 penetrating the first 830 and second 835 surfaces and either a hooking portion 365 or a looping 370 portion of a removable attachment device 375 affixed to one of the first 830 or second 835 surfaces. The portion 365, 370 provides a mechanism for removably attaching the support tab 825 to the antispasticity aid device 10. An elastic chord 840 is provided. The elastic chord 840 has a first end 845, a second end 850 and is attached at the first end 845 to the support tab 825 through the aperture 840. The elastic chord 840 has a mechanism 852 at the second end 850 for forming a loop 855 adjacent to the second end 850. The loop 855 serves to attach the elastic chord 840 to a support fixture 860 whereby, when the antispasticity aid device 10 is attached to a hand 30 of a stroke victim 170, the antispasticity aid device 10 is attached to the support tab 825 and the loop 855 is attached to the fixture 860, the hand 30 and arm 280 of the stroke victim 170 will be suspended for ease of washing.

(26) In yet another variant, as shown in FIG. 16, the sixth accessory 820 is comprised of a weakened portion 870 in the elastic chord 840. The weakened portion 870 provides a safety feature 875 for the stroke victim 170 in the event the stroke victim 170 should fall. The safety feature 875 prevents the stroke victim 170 from being suspended by the sixth accessory 820.

(27) In still a further variant, as shown in FIG. 17, a coupling 872 in the elastic chord 840 is provided. The coupling 872 has an attaching portion 875 and a receiving portion 880. The attaching portion 875 is affixed to an upper end 885 of a lower portion 890 of the elastic chord 840 and has a head section 895 and a reduced cross-section neck section 900 located below the head section 895. The receiving portion 880 is affixed to a lower end 905 of an upper portion 910 of the elastic chord 840 having a cavity 915. The cavity 915 is sized and shaped to frictionally fit over the attaching portion 875 and has a resilient surrounding lower rim 920. The rim 920 is sized and shaped to fit into the neck section 900 whereby, when a downward pressure on the sixth accessory 820 exceeds pressure required to locate the attaching portion 875 in the receiving portion 880, the attaching portion 875 and the receiving portions 880 will separate. This provides a safety feature 930 for a stroke victim 170 using the sixth accessory 820.

(28) In yet a further variant, as shown in FIG. 18 and FIG. 18A, a seventh accessory 935 is provided. The seventh accessory 935 is comprised of a resilient arm support member 940. The arm support member 940 has a first end 945, a second end 950 and is formed into a loop 955. The loop 955 is joined by an intermediate bridging member 960. The resilient arm support member 940 is sized and shaped to fit frictionally over a wheelchair arm 965 and to provide a channel 970 at an upper surface 975 suitable for resting of a stroke victim's arm 280. At least one retaining strap 980 is provided. The retaining strap 980 has a first portion 985 and a second portion 990. Each of the portions 985, 990 are attached to an outer edge 995 of the loop 955 and has either a looping means 1000 or a hooking means 1005 attached to the portions 985, 990 to permit the retaining strap 980 to be fastened over an arm 280 of a stroke victim 170.

(29) In still a further variant, as shown in FIG. 19, a hand support platform 1010 is provided. The hand support platform 1010 is attached to at least one end 945, 950 of the loop 955 and is sized and shaped to fit beneath the antispasticity aid device 10. The hand support platform 1010 has a series of slots 1015 for accepting retaining straps 980 to hold the antispasticity aid device 10 to the hand support platform 1010.

Figure 20:
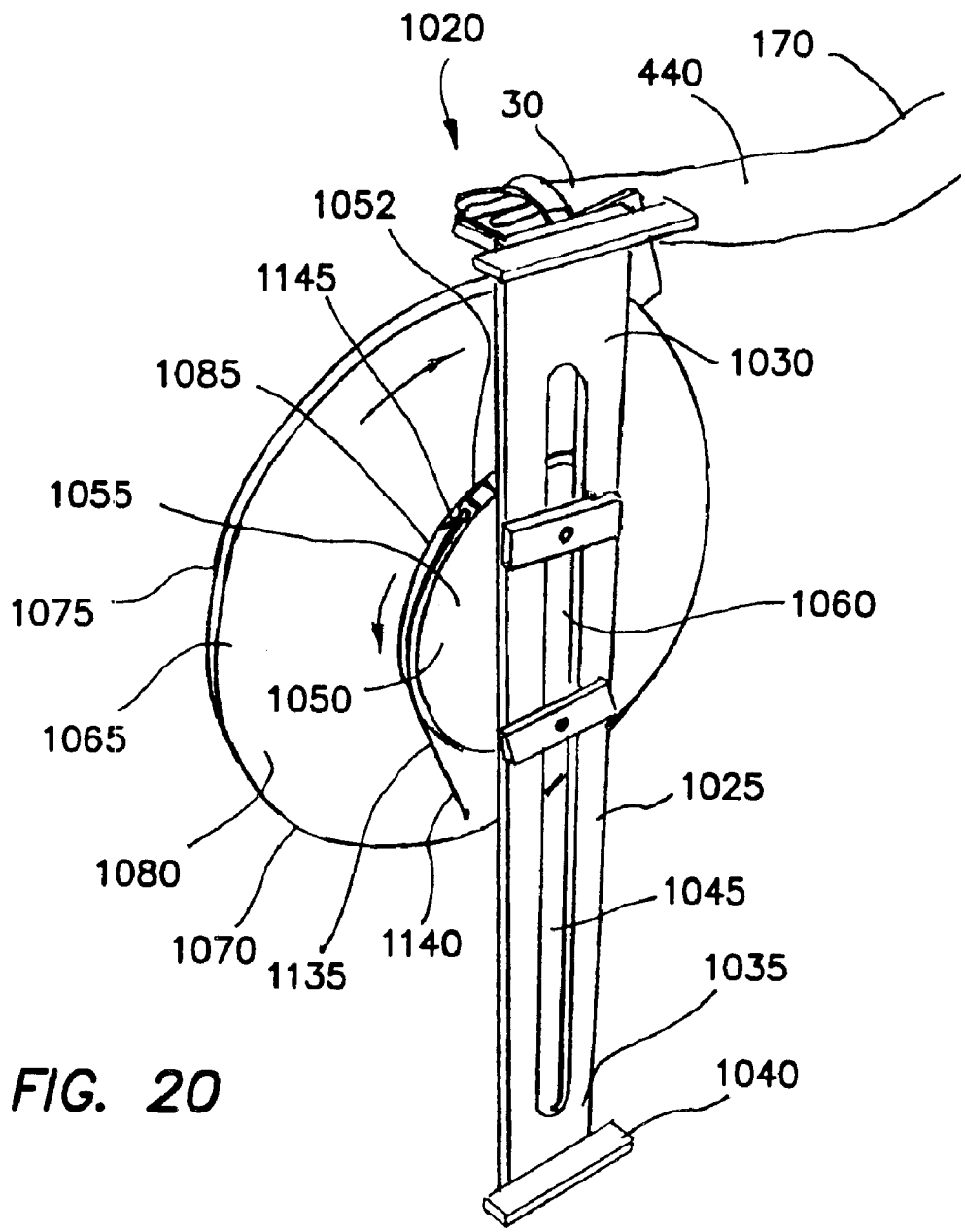
FIG. 20 is a rear perspective view of the eighth accessory illustrating the mounting structure, the bearing mount, the bearing and the planar positioning member.
Figure 21:
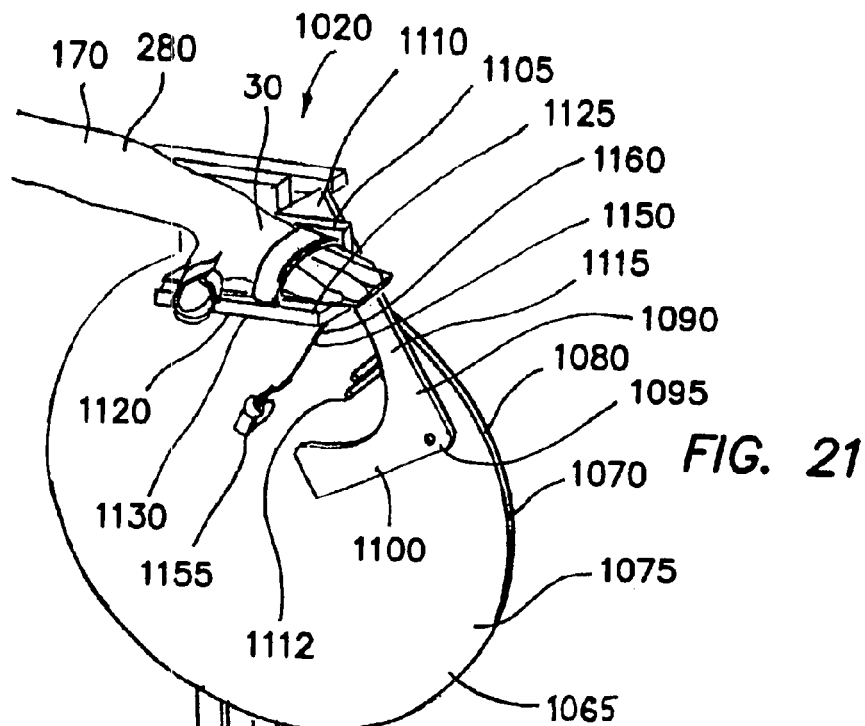
FIG. 21 is a front perspective view of the eighth accessory illustrating the positioning member, the L-shaped control bracket, the control bracket, the stop pin and the antispasticity aid support member.
Figure 21A:
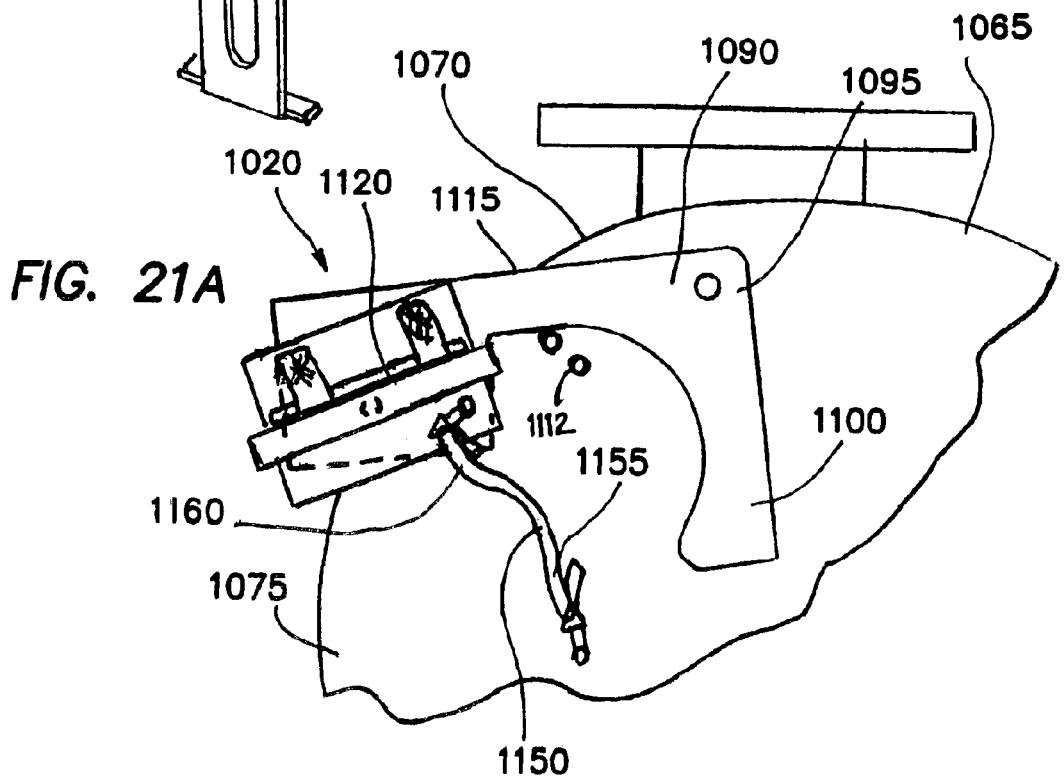
FIG. 21A is a detailed side elevational view of the eighth accessory illustrating the antiplasticity aid support member, the second elastic member, the control bracket, the L-shaped control bracket and the positioning member.

(30) In another variant, as shown in FIG. 20, FIG. 21 and FIG. 21A, an eighth accessory 1020 is provided. The eighth accessory 1020 is comprised of a vertically oriented mounting structure 1025. The mounting structure 1025 has an upper end 1030, a lower end 1035, a support base 1040 located at the lower end 1035 and a central adjusting tract 1045. A bearing mount 1050 is provided. The bearing mount 1050 is slidably affixed to the central adjusting track 1045 and has a curved exterior edge 1052. A bearing 1055 is provided. The bearing 1055 is affixed to a center 1060 of the bearing mount 1050. A planar positioning member 1065 is provided. The positioning member 1065 has a perimeter 1070, a front surface 1075, a rear surface 1080 and is affixed to the bearing 1055 at a center portion 1085 of the rear surface 1080. A planar, L-shaped control bracket 1090 is provided. The control bracket 1090 is pivotally mounted adjacent to a corner 1095 of the L-shape 1100 to the front surface 1075 of the positioning member 1050 adjacent to the perimeter 1070. The control bracket 1090 has a control bracket bearing 1105 mounted at one end 1110 of the L-shape 1100. At least one stop pin 1112 is provided. The stop pin 1112 is mounted to the front surface 1075 of the positioning member 1065 and is located between arms 1115 of the L-shaped control bracket 1090. An antispasticity aid support member 1120 is provided. The support member 1120 has an upper surface 1125 and a lower surface 1130. The support member 1120 is pivotally mounted to the control bracket bearing 1105 and is sized and shaped to support the antispasticity aid device 10. The support member 1120 has either a hooking portion 365 or a looping portion 370 of a removable attachment device 375 affixed to the upper surface 1125 of the support member 1130 for attachment to the antispasticity aid device 10. A first elastic member 1135 is provided. The first elastic member 1135 has a first end 1140 and a second end 1145. The first elastic member 1135 is attached at the first end 1140 to the rear surface 1080 of the planar positioning member 1065 adjacent to the perimeter 1070 and is attached at the second end 1145 to the curved exterior edge 1052 of the bearing mount 1050 whereby, when the antispasticity aid device 10 is attached to a hand 30 of a stroke victim 170 and the antispasticity aid device 10 is attached to the support member 1120, the eighth accessory 1020 will provide a mechanism for exercising arm muscles 440 of the stroke victim 170, permitting rising extension of the arm muscles 440.

(31) In yet another variant, as shown in FIG. 21 and FIG. 21A, a second elastic member 1150 is provided. The elastic member 1150 has a first end 1155 and a second end 1160. The elastic member 1150 is attached at the first end 1155 to the front surface 1075 of the planar positioning member 1065 inward from the perimeter 1070 and is attached at the second end 1160 to the support member 1120. This provides additional stability for the arm 280 of the stroke victim 170 as the eighth accessory 1020 is used for exercising the arm 280 of the stroke victim 170.

Figure 22:
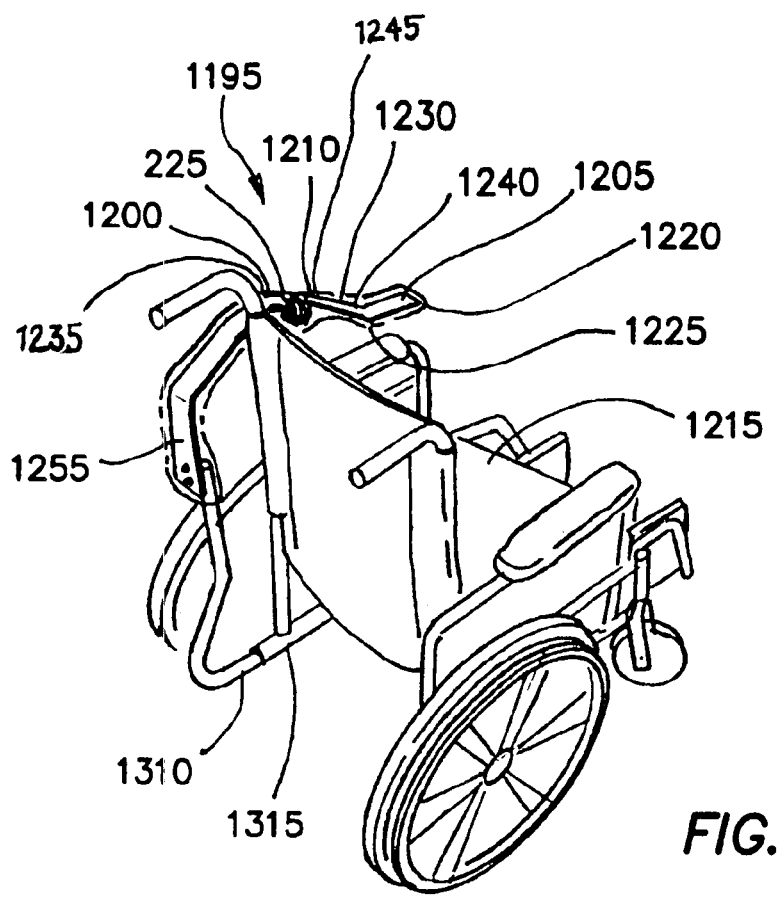
FIG. 22 is a rear perspective view of the ninth accessory illustrating the support platform attached to a wheelchair.
Figure 23:
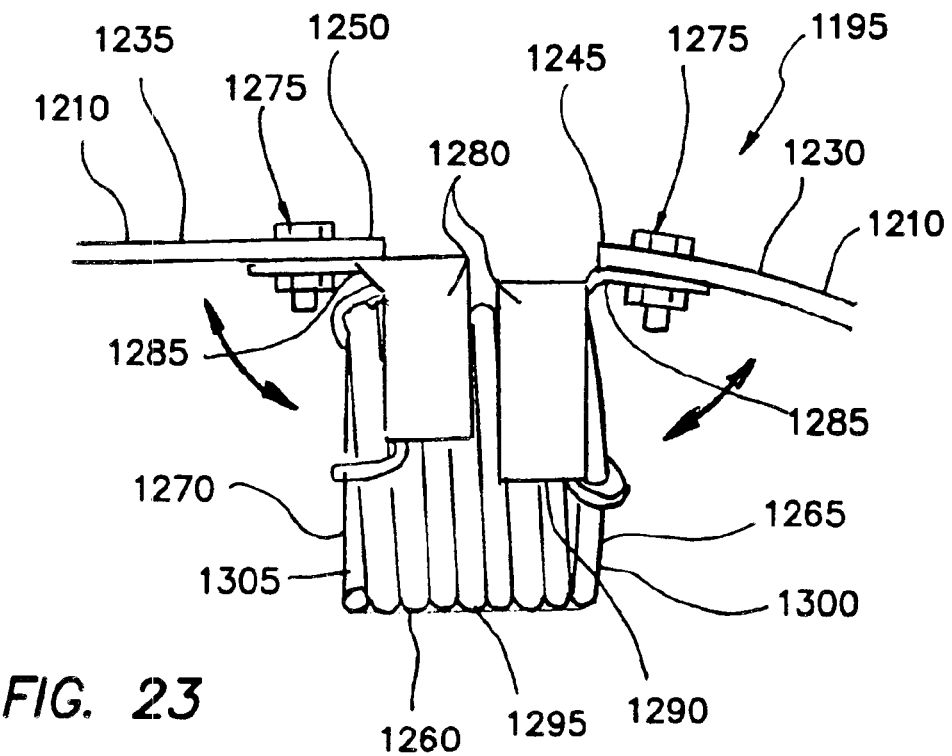
FIG. 23 is a detailed side elevational view of the ninth accessory illustrating the first and second section of the arm support section, the elastic element and the means for attaching the front end of the elastic element to the second end of he first section of the arm support section and the rearward end of the elastic element to the first end of the second section of the arm support section.

(32) In still a further variant, as shown in FIG. 22 and FIG. 23, a ninth accessory 1195 is provided. The ninth accessory 1195 has a support platform 1200. The support platform 1200 is formed of planar semi-rigid, resilient material 225 and has a hand-support section 1205 and an arm support section 1210 and is attached to a wheelchair 1215. The hand-support section 1205 has a distal end 1220 and a proximate end 1225 and is sized and shaped to support the antispasticity aid device 10. The arm support section 1210 has a first section 1230 and a second section 1235. The first section 1230 has a first end 1240 and a second end 1245. The second section 1235 has a first end 1250 and a second end 1255. The first section 1230 of the arm support section 1210 is attached at the first end 1240 to the proximate end 1225 of the hand-support section 1205. An elastic element 1260 is provided. The elastic element 1260 has a front end 1265 and a rearward end 1270. The front end 1265 of the elastic element 1260 is attached to the second end 1245 of the first section 1230 of the arm support section 1210 and the rearward end 1270 of the elastic element 1260 is attached to the first end 1250 of the second section 1235 of the arm support section 1210. Whereby, when the ninth accessory 1195 is attached to the antispasticity aid device 10 and the antispasticity aid device 10 is attached to the hand 30 of a stroke victim 170, the ninth accessory 1195 will permit the stroke victim 170 to apply force against the elastic element 1260 to provide physical therapy for arm muscles 440 of the stroke victim 170.

(33) In another variant, as shown in FIG. 22 and FIG. 23, a means 1275 for attaching the front end 1265 of the elastic element 1260 to the second end 1245 of the first section 1230 of the arm support section 1210 and the rearward end 1270 of the elastic element 1260 to the first end 1250 of the second section 1235 of the arm support section 1210 is provided.

(34) In still another variant, as shown in FIG. 23, at least one bracket 1280 is provided. The bracket 1280 has a first end 1285, a second end 1290 and is attached to either the second end 1245 of the first section 1230 of the arm support section 1210 or the first end 1250 of the second section 1235 of the arm support section 1210 to the first end 1285 of the bracket 1280.

(35) In a further variant, as shown in FIG. 22 and FIG. 23, an extension spring 1295 is provided. The extension spring 1295 has a front end 1300 and a rearward end 1305. The front end 1300 of the extension spring 1295 is attached to the second end 1245 of the first section 1230 of the arm support section 1210 and the rearward end 1305 of the extension spring 1295 is attached to the first end 1250 of the second section 1235 of the arm support section 1210.

(36) In yet another variant, as shown in FIG. 22, a mechanism 1310 of attaching the support platform 1200 at the second end 1255 of the second section 1235 of the arm support section 1210 to a hollow tube 1315 at the rear of the wheelchair 1215 is provided.

Figure 24:
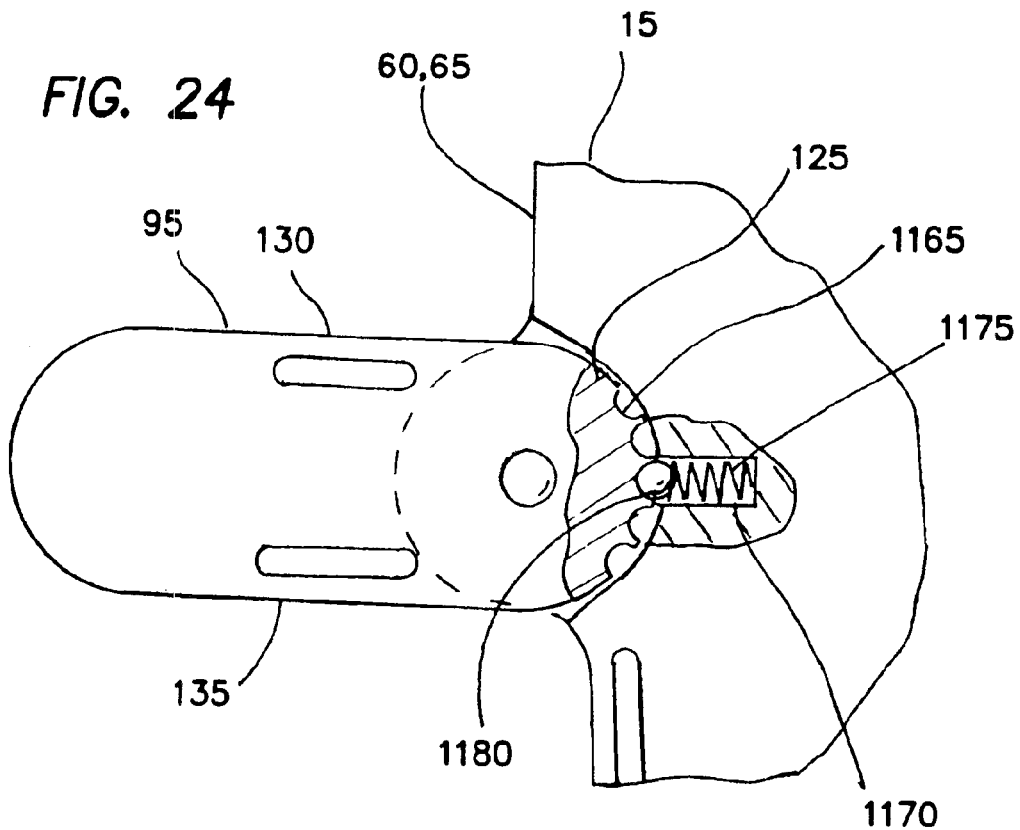
FIG. 24 is partial cross-sectional plan view of the thumb-mounting member illustrating the plurality of detents, the ball channel, the compression spring and the positioning ball.

(37) In still a further variant, as shown in FIG. 24, a plurality of detents 1165 is provided. The detents 1165 are located at the rear edge 125 of the thumb-mounting member 95. A ball channel 1170 is provided. The ball channel 1170 is located in either the first side edge 60 or the second side edge 65 of the hand-mounting member 15. The ball channel 1170 has a compression spring 1175 located within the channel 1170. A positioning ball 1180 is provided. The ball 1180 is sized and shaped to fit slidably within the channel 1170 and to fit within the detents 1165. The ball 1180 is maintained in one of the detents 1165 by the compression spring 1175 whereby, when pressure is applied to the side edge 130, 135 of the thumb-mounting member 95, the ball 1180 will be moved from one detent 1165 to the next. The compression spring 1175 tends to maintain a position of the thumb-mounting member 95 with respect to the hand-mounting member 15.

Figure 25:
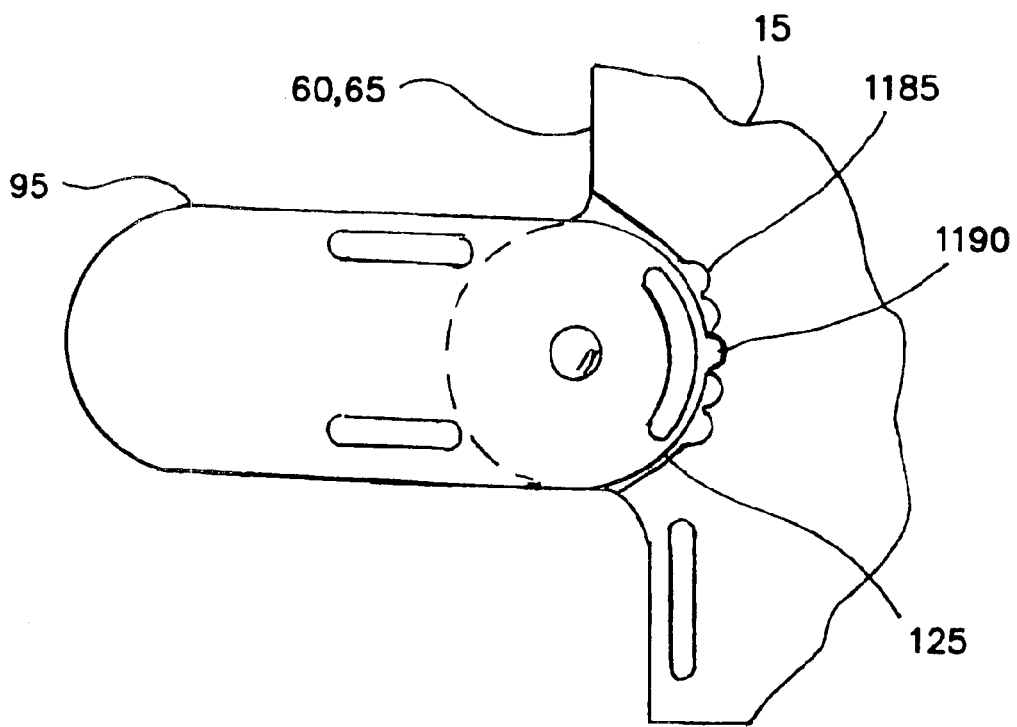
FIG. 25 is a partial cross-sectional plan view of the thumb-mounting member illustrating the plurality of notches and the protruding finger.

(38) In another variant, as shown in FIG. 25, a plurality of notches 1185 is provided. The notches 1185 are located at either the first side edge 60 or the second side edge 65 of the hand-mounting member 15. A protruding finger 1190 is provided. The protruding finger 1190 is located at the rear edge 125 of the thumb-mounting member 95 and is sized and shaped to removably engage any one of the notches 1185 whereby, when the protruding finger 1190 is located in one of the notches 1185, the finger 1190 will maintain a position of the thumb-mounting member 95 with respect to the hand-mounting member 15.

Figure 10A:
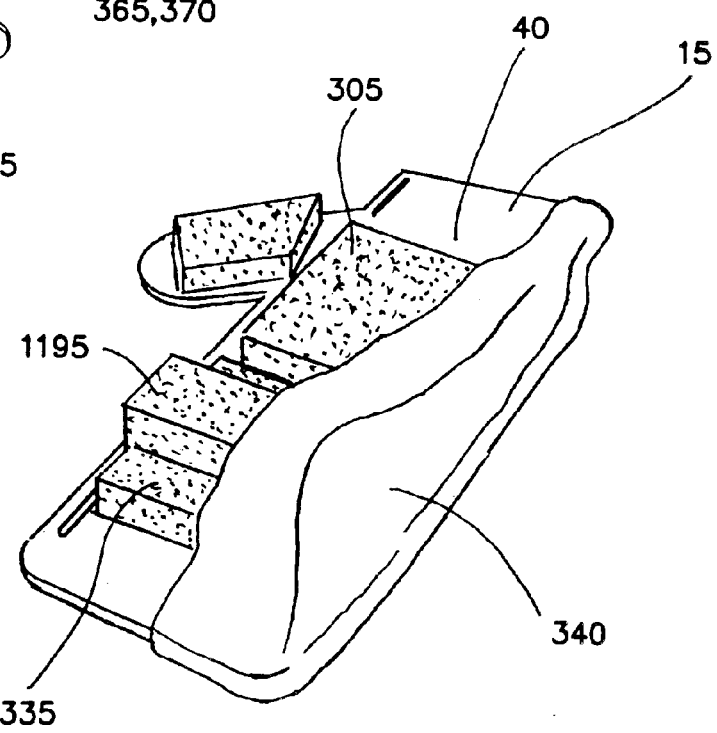
FIG. 10A is a perspective view of the planar hand-mounting member illustrating the raised padding portion attached on the upper surface and the washable material covering the planar hand-mounting member.

(39) In still another variant, as shown in FIG. 10A and FIG. 18A, a raised padding portion 1195 is provided. The raised padding portion 1195 is formed of resilient padding material 305 and is sized and shaped to fit over an upper surface 40 of the planar hand-mounting member 15. Whereby, when the raised padding portion 1195 is fit over the upper surface 40 of the planar hand-mounting member 15 and the raised padding portion 1195 is attached to a hand 30 of a stroke victim 170, the knuckles 1200 of the stroke victim 170 will be elevated above the fingertips 1205 of the stroke victim 170 thereby allowing the hand 30 of the stroke victim 170 to be comfortably positioned on the planar hand-mounting member 15.

(40) In yet still a further variant, as shown in FIG. 10A, the raised padding portion 1195 is formed of an FDA approved foam material 335.

(41) In still a further variant, as shown in FIG. 10A, the planar hand-mounting member 15 is covered with a washable material 340.

(42) In a final variant, as shown in FIG. 10A, the washable material 340 is removable and replaceable.

What is claimed is:

1. An antispasticity aid device, comprising:
   a planar hand-mounting member, said hand-mounting member being formed of rigid material and being sized and shaped to extend beyond outer dimensions of a human hand without a thumb;
   said hand-mounting member having an upper surface, a lower surface, a front edge, a rear edge, a first side edge and a second side edge;
   said hand-mounting member having at least two first fastening slots disposed adjacent said first and second side edges, respectively;
   a first restraining strap, said first strap being sized and shaped to fit slidably through said first fastening slots and having a means for adjusting a length of said first strap;
   a thumb-mounting member, said thumb-mounting member being formed of rigid material and being sized and shaped to extend beyond outer dimensions of a human thumb;
   said thumb-mounting member having an upper surface, a lower surface, a front edge, a rear edge, a first side edge and a second side edge;
   said thumb-mounting member having at least two second fastening slots disposed adjacent said first and said second side edges of said thumb-mounting member, respectively;
   a second restraining strap, said second strap being sized and shaped to fit slidably through said second fastening slots and having a means for adjusting a length of said second strap;
   said thumb-mounting member being rotatably attached at its rear edge to said first side edge of said hand mounting member, permitting said thumb-mounting member to rotate through an arc in the plane of said hand mounting member; and
   whereby, when a hand of a stroke victim is placed upon said hand-mounting member, said first restraining strap is disposed over said hand and through said first fastening slots, said length of said first restraining strap is adjusted to hold said hand in firm contact with said hand mounting member and when a thumb of stroke victim is placed upon said thumb-mounting member, said second restraining strap is disposed over said thumb and through said second fastening slots, said length of said second restraining strap is adjusted to hold said thumb in firm contact with said thumb mounting member, said thumb-mounting member is adjustable with respect to said hand-mounting member for comfort of said stroke victim.

2. The antispasticity aid device, as described in claim 1, wherein said means for adjusting said length of either of said first and said second restraining straps further comprises:

a hooking element disposed adjacent a first end of said restraining strap;

a looping element extending from a second end of said restraining strap toward said first end; and whereby, when said hooking element is attached to said looping element at different points along said length of said restraining strap, said length of either of said first and said second restraining strap is adjusted.

3. The antispasticity aid device, as described in claim 1, wherein said thumb-mounting member is lockable in a plurality of positions about a point where it is rotatably attached at its rear edge to said first side edge of said hand-mounting member.

4. A first accessory for use with either of said antispasticity aid device as described in claim 1 and said antispasticity aid device as described in claim 1 having a fixed thumb-mounting member, comprising:

an arm-rest portion, said arm-rest portion being formed of planar semi-rigid, resilient material, having a hand-shaped section and an extension section;

said hand-shaped section having a distal end and a proximate end and being sized and shaped to support said antispasticity aid device;

said extension section having a first end and a second end and having a length less than a distance from an armpit to a wrist of a stroke victim, and being attached at said first end to said proximate end of said hand-shaped section;

said first accessory being attached to said antispasticity aid device using either of said first and said second fastening straps and said hooking and said looping fastening portions; and whereby, when said first accessory is attached to said antispasticity aid device and said antispasticity aid device is attached to the hand of a stroke victim, an arm of said stroke victim may be comfortably positioned on an arm of an armchair or sofa.

5. The first accessory as described in claim 4, further comprising:

an upper padding portion, said upper padding portion being formed of resilient padding material and being sized and shaped to fit over an upper surface of said extension section of said arm-rest portion; and whereby, when said first accessory is attached to said antispasticity aid device, said antispasticity aid device is attached to the hand of a stroke victim and said upper padding portion is positioned over said extension section, said arm of said stroke victim will be more comfortably positioned upon said first accessory.

6. The first accessory as described in claim 4, further comprising:

a lower padding portion, said lower padding portion being formed of resilient padding material and being sized and shaped to fit over a lower surface of said extension section of said arm-rest portion; and whereby, when said first accessory is attached to said antispasticity aid device, said antispasticity aid device is attached to the hand of a stroke victim and said lower padding portion is positioned under said extension section, said arm of said stroke victim will be more comfortably positioned upon said first accessory.

7. The first accessory as described in claim 4, wherein said extension section tapers in a vertical plane from said first end to said second end, thereby lowering a point of contact adjacent an armpit of said stroke victim.

8. The first accessory as described in claim 5, wherein said upper padding portion is formed of an foam material.

9. The first accessory as described in claim 6, wherein said lower padding portion is formed of an foam material.

10. The first accessory as described in claim 5 or claim 6, wherein said extension section is covered with washable material.

11. The first accessory as described in claim 10, wherein said washable material is removable and replaceable.

12. The first accessory as described in claim 4, wherein said second end of said extension section further comprises a padded portion, said padded portion being sized and shaped to fit comfortably into said armpit of a stroke victim.

13. The first accessory as described in claim 4, wherein said extension section further comprises at least one pair of attachment slots, said attachment slots being disposed along side edges of said extension section between said first end and said second end and being sized and shaped to accommodate an attachment strap.

14. The first accessory as described in claim 4, further comprising:

either of a hooking portion and a looping portion of a removable attachment device, said portion being affixed to an upper surface of said hand shaped section; and said portion providing a mechanism for removably attaching to said antispasticity aid device.

15. A second accessory for use with either of said antispasticity aid device as described in claim 1 and said antispasticity aid device as described in claim 1 having a fixed thumb-mounting member, comprising:

a support platform, said support platform being formed of planar semi-rigid, resilient material, having an upper surface, having a lower surface and having a hand-support section and an arm support section;

said hand support section having a distal end and a proximate end and being sized and shaped to support said antispasticity aid device;

said arm support section having a first end and a second end and having a length less than a distance from an armpit to a wrist of a stroke victim, and being attached at said first end to said proximate end of said hand-support section;

said second accessory being attached to said antispasticity aid device using either of said first and said second fastening straps and said hooking and said looping fastening portions;

a planar base, said planar base having an upper surface, a lower surface and being sized and shaped to fit beneath said support platform;

a leaf spring, said leaf spring having an upper section and a lower section and being formed with an acute angle between said upper section and said lower section;

said upper section being affixed to said lower surface of said support platform and said lower section being affixed to said upper surface of said planar base; and whereby, when said second accessory is attached to said antispasticity aid device and said antispasticity aid device is attached to the hand of a stroke victim, said second accessory will permit said stroke victim to apply force against said leaf spring to provide physical therapy for arm muscles of said stroke victim.

16. The second accessory as described in claim 15, further comprising padding material affixed to said upper surface of said support platform.

17. The second accessory as described in claim 15, further comprising padding material affixed to said lower surface of said support platform.

18. The second accessory as described in claim 15, further comprising a compression spring, said compression spring being disposed between said upper surface of said planar base and an underside of said hand-support section of said support platform, thereby providing additional resistance to said stroke victim seeking physical therapy.

19. The antispasticity aid device, as described in claim 1, further comprising:
   at least one mounting bracket, said mounting bracket being affixed to said lower surface of said planar hand-mounting member and being formed of resilient material;
   said mounting bracket being sized and shaped to removably attach to either of a top bar of a walker and a cane handle; and
   whereby the antispasticity aid device is easily attachable to either of said walker and said cane handle by a stroke victim not able to adequately grip such devices with a hand.

20. The antispasticity aid device, as described in claim 1, further comprising:
   either of a hooking portion and a looping portion of a removable attachment device, said portion being affixed to said lower surface of said planar hand-mounting member; and
   said portion providing a mechanism for removably attaching said antispasticity aid device to accessory devices.

21. A third accessory for use with either of said antispasticity aid device as described in claim 20 and said antispasticity aid device as described in claim 20 having a fixed thumb-mounting member, comprising:
   an arm-rest portion, said arm-rest portion being formed of planar semi-rigid, resilient material, having a hand-shaped section and an extension section;
   said hand shaped section having an upper surface, a lower surface, a distal end and a proximate end and being sized and shaped to support said antispasticity aid device;
   said hand shaped section having either of a looping portion and a hooking portion of a removable attachment device affixed to said upper surface for attachment to said antispasticity aid device
   said extension section having a first end and a second end and having a length greater than a distance from a back of a wrist of a stroke victim, and being attached at said first end to said proximate end of said hand-shaped section;
   at least one reinforcing element, said reinforcing element being formed of resilient material and being disposed within said arm-rest portion and extending from said second end of said extension section to at least into said hand shaped section;
   a mounting hinge, said mounting hinge having a first portion and a second portion and being attached at said first portion to said reinforcing element adjacent said second end of said extension section and being attached at said second portion to a wall adjacent either of a toilet and a bathtub;
   said mounting hinge maintaining said third accessory in a position orthogonal to said wall; and
   whereby, when attached to said wall, said third accessory will provide a comfortable location for a stroke victim to rest an arm when using either of said bathtub and said toilet.

22. A fourth accessory for use with either of said antispasticity aid device as described in claim 1 and said antispasticity aid device as described in claim 1 having a fixed thumb-mounting member, comprising:
   a concave rest portion, said rest portion having an upper surface and a lower surface and being sized and shaped to accommodate an arm of a stroke victim using one of said antispasticity aid devices on said upper surface;
   a support portion, said support portion having a top surface, a bottom surface, being of a length sufficient to support said rest portion, being attached at said top surface to said lower surface of said rest portion and being of a height sufficient to maintain said rest portion at a desired height;
   an attachment portion, said attachment portion having an upper surface and a lower surface, being attached at said upper surface to said bottom surface of said support portion and being sized and shaped to fit frictionally over either of an arm of a chair and a sofa at said lower surface; and
   whereby, when fitted to either of said arm of a chair or a sofa, said fourth accessory will provide a comfortable and secure rest location for a stroke victim's arm.

23. A fourth accessory for use with either of said antispasticity aid device as described in claim 20 and said antispasticity aid device as described in claim 20 having a fixed thumb-mounting member, comprising:
   a walker, said walker having two pairs of downward pointing legs, each of said pairs attaching at upper ends to a top cross bar, at least one leg of each pair being hingedly joined to at least one connecting bar;
   a support platform, said support platform being pivotally attached to a bracket, said bracket being attached to said at least one connecting bar;
   said platform having a first end for supporting a wrist of a stroke victim and a second end for supporting said antispasticity aid device, said second end having either of a hooking portion and a looping portion of a removable attachment device positioned upon an upper surface for removable attachment to said antispasticity aid device;
   at least one elastic member, said elastic member being disposed between said bracket and an underside of said support platform; and
   said elastic member providing resistive stability for said platform when supporting a hand and arm of a stroke victim.

24. A fifth accessory for use with either of said antispasticity aid device as described in claim 19 and said antispasticity aid device as described in claim 19 having a fixed thumb-mounting member, comprising:
   a floor bracket, said floor bracket having an upper surface, a lower surface, a pivotal mounting bracket affixed to said upper surface and a non-slip finish on said lower surface;

an adjustable support shaft, said support shaft having an upper portion, a lower portion, said lower portion fitting slidably within said upper portion and having a clamping mechanism for adjustably fastening said upper portion to said lower portion at a variety of heights;

said lower portion having a fitting affixed at a lower end, said fitting being sized and shaped to fit said pivotal mounting bracket;

said upper portion having a handle at an upper end, said handle being sized and shaped to accept said mounting bracket of said antispasticity aid device; and whereby when said antispasticity aid device is removably affixed to said handle, a stroke victim will use said fifth accessory to exercise the arm and shoulder muscles.

25. A sixth accessory for use with either of said antispasticity aid device as described in claim 20 and said antispasticity aid device as described in claim 20 having a fixed thumb-mounting member, comprising:

a support tab, said support tab having a first surface and a second surface, an aperture penetrating said first and second surfaces, either of a hooking portion and a looping portion of a removable attachment device affixed to one of said first and second surfaces;

said portion providing a mechanism for removably attaching said support tab to said antispasticity aid device;

an elastic chord, said elastic chord having a first end, a second end and being attached at said first end to said support tab through said aperture and having a mechanism at said second end for forming a loop adjacent said second end;

said loop serving to attach said elastic chord to a support fixture; and whereby, when said antispasticity aid device is attached to a hand of a stroke victim and said antispasticity aid device is attached to said support tab and said loop is attached to said fixture, said hand and arm of said stroke victim will be suspended for ease of washing.

26. The sixth accessory, as described in claim 25, further comprising a weakened portion in said elastic chord, said weakened portion providing a safety feature for said stroke victim in the event said stroke victim should fall, the safety feature preventing said stroke victim from being suspended by said sixth accessory.

27. The sixth accessory, as described in claim 25, further comprising:

a coupling in said elastic chord, said coupling having an attaching portion and a receiving portion;

said attaching portion being affixed to an upper end of a lower portion of said elastic chord and having a head section and a reduced cross-section neck section disposed below said head section;

said receiving portion being affixed to a lower end of an upper portion of said elastic chord having a cavity, said cavity being sized and shaped to frictionally fit over said attaching portion and having a resilient surrounding lower rim, said rim being sized and shaped to fit into said neck section; and whereby, when a downward pressure on said sixth accessory exceeds pressure required to locate said attaching portion in said receiving portion, said attaching portion and said receiving portions will separate, providing a safety feature for a stroke victim using said sixth accessory.

28. A seventh accessory for use with either of said antispasticity aid device as described in claim 1 and said antispasticity aid device as described in claim 1 having a fixed thumb-mounting member, comprising:

a resilient arm support member, said arm support member having a first end, a second end and being formed into a loop, said loop being joined by an intermediate bridging member;

said resilient arm member being sized and shaped to fit frictionally over a wheelchair arm and to provide a channel at an upper surface suitable for resting of a stroke victim's arm;

at least one retaining strap, said retaining strap having a first portion and a second portion, each of said portions being attached to an outer edge of said loop and having either of a looping means and a hooking means attached to said portions to permit said retaining strap to be fastened over an arm of a stroke victim.

29. The seventh accessory, as described in claim 28, further comprising a hand support platform, said hand support platform being attached to at least one end of said loop and being sized and shaped to fit beneath said antispasticity aid device, and having a series of slots for accepting retaining straps to hold said antispasticity aid device to said hand support platform.

30. An eighth accessory for use with either of said antispasticity aid device as described in claim 20 and said antispasticity aid device as described in claim 20 having a fixed thumb-mounting member, comprising:

a vertically oriented mounting structure, said mounting structure having an upper end, a lower end, a support base disposed at said lower end and a central adjusting tract;

a bearing mount, said bearing mount being slidably affixed to said central adjusting track and having a curved exterior edge;

a bearing, said bearing being affixed to a center of said bearing mount;

a planar positioning member, said positioning member having a perimeter, a front surface, a rear surface and being affixed to said bearing at a center portion of said rear surface;

a planar, L-shaped control bracket, said control bracket being pivotally mounted adjacent a corner of said L-shape to said front surface of said positioning member adjacent said perimeter, and having a control bracket bearing mounted at one end of said L-shape;

at least one stop pin, said stop pin being mounted to said front surface of said positioning member and being disposed between arms of said L-shaped control bracket;

an antispasticity aid support member, said support member having an upper surface and a lower surface, being pivotally mounted to said control bracket bearing, being sized and shaped to support said stroke victim aid, and having either of a hooking portion and a looping portion of a removable attachment device affixed to said upper surface of said support member for attachment to said antispasticity aid device;

a first elastic member, said first elastic member having a first end and a second end and being attached at said first end to said rear surface of said planar positioning member adjacent said perimeter and being attached at said second end to said curved exterior edge of said bearing mount; and whereby, when said antispasticity aid device is attached to a hand of a stroke victim and said antispasticity aid device is attached to said support member, said eighth accessory will provide a mechanism for exercising arm muscles of said stroke victim, permitting rising extension of said arm muscles.

31. The eighth accessory, as described in claim 30, further comprising a second elastic member, said second elastic member having a first end and a second end and being attached at said first end to said front surface of said planar positioning member inward from said perimeter and being attached at said second end to said support member, thereby providing additional stability for said arm of said stroke victim as said eighth accessory is used for exercising said arm of said stroke victim.

32. A ninth accessory for use with either of said antispasticity aid device as described in claim 1 and said antispasticity aid device as described in claim 1 having a fixed thumb-mounting member, comprising:
  a support platform, said support platform being formed of planar semi-rigid, resilient material, having a hand-support section and an arm support section, and being attached to a wheelchair;
  said hand support section having a distal end and a proximate end and being sized and shaped to support said antispasticity aid device;
  said arm support section having a first section and a second section, said first section having a first end and a second end, said second section having a first end and a second end, and said first section of said arm support section being attached at said first end to said proximate end of said hand support section;
  an elastic element, said elastic element having a front end and a rearward end, said front end of said elastic element being attached to said second end of said first section of said arm support section, and said rearward end of said elastic element being attached to said first end of said second section of said arm support section;
  whereby, when said ninth accessory is attached to said antispasticity aid device and said antispasticity aid device is attached to the hand of a stroke victim, said ninth accessory will permit said stroke victim to apply force against said elastic element to provide physical therapy for arm muscles of said stroke victim.

33. The ninth accessory as described in claim 32, further comprising a means for attaching said front end of said elastic element to said second end of said first section of said arm support section and said rearward end of said elastic element to said first end of said second section of said arm support section.

34. The ninth accessory as described in claim 33, wherein the means for attaching said front end of said elastic element to said second end of said first section of said arm support section and said rearward end of said elastic element to said first end of said second section of said arm support section further comprise:
  at least one bracket, said bracket having a first end and a second end, and being attached to either of said second end of said first section of said arm support section and said first section of said second section of said arm support section to said first end of said bracket.

35. The ninth accessory as described in claim 32, further comprising an extension spring, said extension spring having a front end and a rearward end, and said front end of said extension spring being attached to said second end of said first section of said arm support section, and said rearward end of said extension spring being attached to said first end of said second section of said arm support section.

36. The ninth accessory as described in claim 32, further comprising a mechanism of attaching said support platform at said second end of said second section of said arm support section to a hollow tube at the rear of said wheelchair.

37. The antispasticity aid device, as described in claim 3, further comprising:
  a plurality of detents, said detents being disposed at said rear edge of said thumb-mounting member;
  a ball channel, said ball channel being disposed in either of said first side edge and said second side edge of said hand-mounting member, and having a compression spring disposed within said channel;
  a positioning ball, said ball being sized and shaped to fit slidably within said channel and to fit within said detents, said ball being maintained in one of said detents by said compression spring; and
  whereby, when pressure is applied to a side edge of said thumb mounting member, said ball will be moved from one detent to the next, said compression spring tending to maintain a position of said thumb mounting member with respect to said hand mounting member.

38. The antispasticity aid device, as described in claim 3, further comprising:
  a plurality of notches, said notches being disposed at either of said first side edge and said second side edge of said hand-mounting member;
  a protruding finger, said protruding finger being disposed at said rear edge of said thumb-mounting member and being sized and shaped to removably engage any one of said notches; and
  whereby, when said protruding finger is disposed in one of said notches, said finger will maintain a position of said thumb mounting member with respect to said hand mounting member.

39. The planar hand-mounting member, as described in claim 1, further comprising an raised padding portion, said raised padding portion being formed of resilient padding material, and being sized and shaped to fit over an upper surface of said planar hand-mounting member; and
  whereby, when said raised padding portion is fit over said upper surface of said planar hand-mounting member, and said raised padding portion is attached to a hand of a stroke victim, the knuckles of said stroke victim will be elevated above the fingertips of said stroke victim thereby allowing said hand of said stroke victim to be comfortably positioned on said planar hand-mounting member.

40. The planar hand-mounting member, as described in claim 39, wherein said raised padding portion being formed of an foam material.

41. The planar hand-mounting member, as described in claim 39, wherein said planar hand-mounting member being covered with washable material.

42. The planar hand-mounting member, as described in claim 41, wherein said washable material being removable and replaceable.

43. An antispasticity aid device, comprising:
  a planar hand-mounting member, said hand-mounting member being formed of rigid material and being sized and shaped to extend beyond outer dimensions of a human hand without a thumb;
  said hand-mounting member having an upper surface, a lower surface, a front edge, a rear edge, a first side edge and a second side edge;
  said hand-mounting member having at least two first fastening slots disposed adjacent said first and second side edges, respectively;

a first restraining strap, said first strap being sized and shaped to fit slidably through said first fastening slots and having a means for adjusting a length of said first strap;

a thumb-mounting member, said thumb-mounting member being formed of rigid material and being sized and shaped to extend beyond outer dimensions of a human thumb;

said thumb-mounting member having an upper surface, a lower surface, a front edge, a rear edge, a first side edge and a second side edge;

said thumb-mounting member having at least two second fastening slots disposed adjacent said first and said second side edges of said thumb-mounting member, respectively;

a second restraining strap, said second strap being sized and shaped to fit slidably through said second fastening slots and having a means for adjusting a length of said second strap;

said thumb-mounting member being attached at its rear edge to said first side edge of said hand mounting member;

a first accessory comprising;
  an arm-rest portion, said arm-rest portion being formed of planar semi-rigid, resilient material, having a hand-shaped section and an extension section;
  said hand-shaped section having a distal end and a proximate end and being sized and shaped to support said antispasticity aid device;
  said extension section having a first end and a second end and having a length less than a distance from an armpit to a wrist of a stroke victim, and being attached at said first end to said proximate end of said hand-shaped section; said extension section tapering in a vertical plane from said first end to said second end, thereby lowering a point of contact adjacent an armpit of said stroke victim;

said first accessory being attached to said antispasticity aid device using either of said first and said second fastening straps and said hooking and said looping fastening portions; and whereby, when a hand of a stroke victim is placed upon said hand-mounting member, said first restraining strap is disposed over said hand and through said first fastening slots, said length of said first restraining strap is adjusted to hold said hand in firm contact with said hand mounting member and when a thumb of stroke victim is placed upon said thumb-mounting member, said second restraining strap is disposed over said thumb and through said second fastening slots, said length of said second restraining strap is adjusted to hold said thumb in firm contact with said thumb mounting member, said thumb-mounting member is adjustable with respect to said hand-mounting member for comfort of said stroke victim; and whereby, when said first accessory is attached to said antispasticity aid device and said antispasticity aid device is attached to the hand of a stroke victim, an arm of said stroke victim may be comfortably positioned on an arm of an armchair or sofa.

44. An antispasticity aid device as claimed in claim 43 in which said thumb-mounting member is rotatably attached at its rear edge to said first side edge of said hand mounting member, permitting said thumb-mounting member to rotate through an arc in the plane of said hand mounting member.

45. An antispasticity aid device, comprising:
a planar hand-mounting member, said hand-mounting member being formed of rigid material and being sized and shaped to extend beyond outer dimensions of a human hand without a thumb;

said hand-mounting member having an upper surface, a lower surface, a front edge, a rear edge, a first side edge and a second side edge;

said hand-mounting member having at least two first fastening slots disposed adjacent said first and second side edges, respectively;

a first restraining strap, said first strap being sized and shaped to fit slidably through said first fastening slots and having a means for adjusting a length of said first strap;

a thumb-mounting member, said thumb-mounting member being formed of rigid material and being sized and shaped to extend beyond outer dimensions of a human thumb;

said thumb-mounting member having an upper surface, a lower surface, a front edge, a rear edge, a first side edge and a second side edge;

said thumb-mounting member having at least two second fastening slots disposed adjacent said first and said second side edges of said thumb-mounting member, respectively;

a second restraining strap, said second strap being sized and shaped to fit slidably through said second fastening slots and having a means for adjusting a length of said second strap;

said thumb-mounting member being attached at its rear edge to said first side edge of said hand mounting member;

a first accessory comprising:
  an arm-rest portion, said arm-rest portion being formed of planar semi-rigid, resilient material, having a hand-shaped section and an extension section;
  said hand-shaped section having a distal end and a proximate end and being sized and shaped to support said antispasticity aid device;
  said extension section having a first end and a second end and having a length less than a distance from an armpit to a wrist of a stroke victim, and being attached at said first end to said proximate end of said hand-shaped section; said second end of said extension section further comprising a padded portion, said padded portion being sized and shaped to fit comfortably into said armpit of a stroke victim;

said first accessory being attached to said antispasticity aid device using either of said first and said second fastening straps and said hooking and said looping fastening portions; and whereby, when a hand of a stroke victim is placed upon said hand-mounting member, said first restraining strap is disposed over said hand and through said first fastening slots, said length of said first restraining strap is adjusted to hold said hand in firm contact with said hand mounting member and when a thumb of stroke victim is placed upon said thumb-mounting member, said second restraining strap is disposed over said thumb and through said second fastening slots, said length of said second restraining strap is adjusted to hold said thumb in firm contact with said thumb mounting member, said thumb-mounting member is adjustable with respect to said hand-mounting member for comfort of said stroke victim; and whereby, when said first accessory is attached to said antispasticity aid device and said antispasticity aid device is attached to the hand of a stroke victim, an arm of said stroke victim may be comfortably positioned on an arm of an armchair or sofa.

46. An antispasticity aid device as claimed in claim 45 in which said thumb-mounting member is rotatably attached at its rear edge to said first side edge of said hand mounting member, permitting said thumb-mounting member to rotate through an arc in the plane of said hand mounting member.

47. An antispasticity aid device, comprising:
a planar hand-mounting member, said hand-mounting member being formed of rigid material and being sized and shaped to extend beyond outer dimensions of a human hand without a thumb;
said hand-mounting member having an upper surface, a lower surface, a front edge, a rear edge, a first side edge and a second side edge;
said hand-mounting member having at least two first fastening slots disposed adjacent said first and second side edges, respectively;
a first restraining strap, said first strap being sized and shaped to fit slidably through said first fastening slots and having a means for adjusting a length of said first strap;
a thumb-mounting member, said thumb-mounting member being formed of rigid material and being sized and shaped to extend beyond outer dimensions of a human thumb;
said thumb-mounting member having an upper surface, a lower surface, a front edge, a rear edge, a first side edge and a second side edge;
said thumb-mounting member having at least two second fastening slots disposed adjacent said first and said second side edges of said thumb-mounting member, respectively;
a second restraining strap, said second strap being sized and shaped to fit slidably through said second fastening slots and having a means for adjusting a length of said second strap;
said thumb-mounting member being attached at its rear edge to said first side edge of said hand mounting member;
a second accessory comprising:
a support platform, said support platform being formed of planar semi-rigid, resilient material, having an upper surface, having a lower surface and having a hand-support section and an arm support section;
said hand support section having a distal end and a proximate end and being sized and shaped to support said antispasticity aid device;
said arm support section having a first end and a second end and having a length less than a distance from an armpit to a wrist of a stroke victim, and being attached at said first end to said proximate end of said hand-support section;
a compression spring, said compression spring being disposed between said upper surface of said planar base and an underside of said hand-support section of said support platform, thereby providing additional resistance to said stroke victim seeking physical therapy;
said second accessory being attached to said antispasticity aid device using either of said first and said second fastening straps and said hooking and said looping fastening portions;

a planar base, said planar base having an upper surface, a lower surface and being sized and shaped to fit beneath said support platform;
a leaf spring, said leaf spring having an upper section and a lower section and being formed with an acute angle between said upper section and said lower section;
said upper section being affixed to said lower surface of said support platform and said lower section being affixed to said upper surface of said planar base; and
whereby, when said second accessory is attached to said antispasticity aid device and said antispasticity aid device is attached to the hand of a stroke victim, said second accessory will permit said stroke victim to apply force against said leaf spring to provide physical therapy for arm muscles of said stroke victim; and
whereby, when a hand of a stroke victim is placed upon said hand-mounting member, said first restraining strap is disposed over said hand and through said first fastening slots, said length of said first restraining strap is adjusted to hold said hand in firm contact with said hand mounting member and when a thumb of stroke victim is placed upon said thumb-mounting member, said second restraining strap is disposed over said thumb and through said second fastening slots, said length of said second restraining strap is adjusted to hold said thumb in firm contact with said thumb mounting member, said thumb-mounting member is adjustable with respect to said hand-mounting member for comfort of said stroke victim.

48. An antispasticity aid device as claimed in claim 47 in which said thumb-mounting member is rotatably attached at its rear edge to said first side edge of said hand mounting member, permitting said thumb-mounting member to rotate through an arc in the plane of said hand mounting member.

49. An antispasticity aid device, comprising:
a planar hand-mounting member, said hand-mounting member being formed of rigid material and being sized and shaped to extend beyond outer dimensions of a human hand without a thumb;
said hand-mounting member having an upper surface, a lower surface, a front edge, a rear edge, a first side edge and a second side edge;
said hand-mounting member having at least two first fastening slots disposed adjacent said first and second side edges, respectively;
a first restraining strap, said first strap being sized and shaped to fit slidably through said first fastening slots and having a means for adjusting a length of said first strap;
a thumb-mounting member, said thumb-mounting member being formed of rigid material and being sized and shaped to extend beyond outer dimensions of a human thumb;
said thumb-mounting member having an upper surface, a lower surface, a front edge, a rear edge, a first side edge and a second side edge;
said thumb-mounting member having at least two second fastening slots disposed adjacent said first and said second side edges of said thumb-mounting member, respectively;
a second restraining strap, said second strap being sized and shaped to fit slidably through said second fastening slots and having a means for adjusting a length of said second strap;

said thumb-mounting member being rotatably attached at its rear edge to said first side edge of said band mounting member, permitting said thumb-mounting member to rotate through an arc in the plane of said hand mounting member;

at least one mounting bracket, said mounting bracket being affixed to said lower surface of said planar hand-mounting member and being formed of resilient material;

said mounting bracket being sized and shaped to removably attach to either of a top bar of a walker and a cane handle;

whereby, when a hand of a stroke victim is placed upon said hand-mounting member, said first restraining strap is disposed over said hand and through said first fastening slots, said length of said first restraining strap is adjusted to hold said hand in firm contact with said hand mounting member and when a thumb of stroke victim is placed upon said thumb-mounting member, said second restraining strap is disposed over said thumb and through said second fastening slots, said length of said second restraining strap is adjusted to hold said thumb in firm contact with said thumb mounting member, said thumb-mounting member is adjustable with respect to said hand-mounting member for comfort of said stroke victim; and whereby the antispasticity aid device is easily attachable to either of said walker and said cane handle by a stroke victim not able to adequately grip such devices with a hand.

50. An antispasticity aid device, comprising:

a planar hand-mounting member, said hand-mounting member being formed of rigid material and being sized and shared to extend beyond outer dimensions of a human hand without a thumb;

said hand-mounting member having an upper surface, a lower surface, a front edge, a rear edge, a first side edge and a second side edge;

said hand-mounting member having at least two first fastening slots disposed adjacent said first and second side edges, respectively;

a first restraining strap, said first strap being sized and shaped to fit slidably through said first fastening slots and having a means for adjusting a length of said first strap;

a thumb-mounting member, said thumb-mounting member being formed of rigid material and being sized and shared to extend beyond outer dimensions of a human thumb;

said thumb-mounting member having an upper surface, a lower surface, a front edge, a rear edge, a first side edge and a second side edge;

said thumb-mounting member having at least two second fastening slots disposed adjacent said first and said second side edges of said thumb-mounting member, respectively;

a second restraining strap, said second strap being sized and shaped to fit slidably through said second fastening slots and having a means for adjusting a length of said second strap;

said thumb-mounting member being attached at its rear edge to said first side edge of said hand mounting member;

either of a hooking portion and a looping portion of a removable attachment device, said portion being affixed to said lower surface of said planar hand-mounting member; and said portion providing a mechanism for removably attaching said antispasticity aid device to accessory devices;

a third accessory comprising:

an arm-rest portion, said arm-rest portion being formed of planar semi-rigid, resilient material, having a hand-shaped section and an extension section;

said hand shared section having an upper surface, a lower surface, a distal end and a proximate end and being sized and shaped to support said antispasticity aid device;

said hand shared section having either of a looping portion and a hooking portion of a removable attachment device affixed to said upper surface for attachment to said antispasticity aid device said extension section having a first end and a second end and having a length greater than a distance from a back of a wrist of a stroke victim, and being attached at said first end to said proximate end of said hand-shaped section;

at least one reinforcing element, said reinforcing element being formed of resilient material and being disposed within said arm-rest portion and extending from said second end of said extension section to at least into said hand shaped section;

a mounting hinge, said mounting hinge having a first portion and a second portion and being attached at said first portion to said reinforcing element adjacent said second end of said extension section and being attached at said second portion to a wall adjacent either of a toilet and a bathtub;

said mounting hinge maintaining said third accessory in a position orthogonal to said wall; and whereby, when attached to said wall, said third accessory will provide a comfortable location for a stroke victim to rest an arm when using either of said bathtub and said toilet; and whereby, when a hand of a stroke victim is placed upon said hand-mounting member, said first restraining strap is disposed over said hand and through said first fastening slots, said length of said first restraining strap is adjusted to hold said hand in firm contact with said hand mounting member and when a thumb of stroke victim is placed upon said thumb-mounting member, said second restraining strap is disposed over said thumb and through said second fastening slots, said length of said second restraining strap is adjusted to hold said thumb in firm contact with said thumb mounting member, said thumb-mounting member is adjustable with respect to said hand-mounting member for comfort of said stroke victim.

51. An antispasticity aid device as claimed in claim 50 in which said thumb-mounting member is rotatably attached at its rear edge to said first side edge of said hand mounting member, permitting said thumb-mounting member to rotate through an arc in the plane of said hand mounting member.

52. An antispasticity aid device, comprising:

a planar hand-mounting member, said hand-mounting member being formed of rigid material and being sized and shaped to extend beyond outer dimensions of a human hand without a thumb;

said hand-mounting member having an upper surface, a lower surface, a front edge, a rear edge, a first side edge and a second side edge;

said hand-mounting member having at least two first fastening slots disposed adjacent said first and second side edges, respectively;

a first restraining strap, said first strap being sized and shaped to fit slidably through said first fastening slots and having a means for adjusting a length of said first strap;

a thumb-mounting member, said thumb-mounting member being formed of rigid material and being sized and shaped to extend beyond outer dimensions of a human thumb;

said thumb-mounting member having an upper surface, a lower surface, a front edge, a rear edge, a first side edge and a second side edge;

said thumb-mounting member having at least two second fastening slots disposed adjacent said first and said second side edges of said thumb-mounting member, respectively;

a second restraining strap, said second strap being sized and shaped to fit slidably through said second fastening slots and having a means for adjusting a length of said second strap;

said thumb-mounting member being attached at its rear edge to said first side edge of said hand mounting member;

a fourth accessory comprising:

a concave rest portion, said rest portion having an upper surface and a lower surface and being sized and shaped to accommodate an arm of a stroke victim using one of said antispasticity aid devices on said upper surface;

a support portion, said support portion having a top surface, a bottom surface, being of a length sufficient to support said rest portion, being attached at said top surface to said lower surface of said rest portion and being of a height sufficient to maintain said rest portion at a desired height;

an attachment portion, said attachment portion having an upper surface and a lower surface, being attached at said upper surface to said bottom surface of said support portion and being sized and shaped to fit frictionally over either of an arm of a chair and a sofa at said lower surface; and whereby, when fitted to either of said arm of a chair or a sofa, said fourth accessory will provide a comfortable and secure rest location for a stroke victim's arm; and whereby, when a hand of a stroke victim is placed upon said hand-mounting member, said first restraining strap is disposed over said hand and through said first fastening slots, said length of said first restraining strap is adjusted to hold said hand in firm contact with said hand mounting member and when a thumb of stroke victim is placed upon said thumb-mounting member, said second restraining strap is disposed over said thumb and through said second fastening slots, said length of said second restraining strap is adjusted to hold said thumb in firm contact with said thumb mounting member, said thumb-mounting member is adjustable with respect to said hand-mounting member for comfort of said stroke victim.

53. An antispasticity aid device as claimed in claim 52 in which said thumb-mounting member is rotatably attached at its rear edge to said first side edge of said hand mounting member, permitting said thumb-mounting member to rotate through an arc in the plane of said hand mounting member.

54. An antispasticity aid device, comprising:

a planar hand-mounting member, said hand-mounting member being formed of rigid material and being sized and shaped to extend beyond outer dimensions of a human hand without a thumb;

said hand-mounting member having an upper surface, a lower surface, a front edge, a rear edge, a first side edge and a second side edge;

said hand-mounting member having at least two first fastening slots disposed adjacent said first and second side edges, respectively;

a first restraining strap, said first strap being sized and shaped to fit slidably through said first fastening slots and having a means for adjusting a length of said first strap;

a thumb-mounting member, said thumb-mounting member being formed of rigid material and being sized and shaped to extend beyond outer dimensions of a human thumb;

said thumb-mounting member having an upper surface, a lower surface, a front edge, a rear edge, a first side edge and a second side edge;

said thumb-mounting member having at least two second fastening slots disposed adjacent said first and said second side edges of said thumb-mounting member, respectively;

a second restraining strap, said second strap being sized and shaped to fit slidably through said second fastening slots and having a means for adjusting a length of said second strap;

said thumb-mounting member being attached at its rear edge to said first side edge of said hand mounting member;

either of a hooking portion and a looping portion of a removable attachment device, said portion being affixed to said lower surface of said planar hand-mounting member; and said portion providing a mechanism for removably attaching said antispasticity aid device to accessory devices;

a fourth accessory comprising:

a walker, said walker having two pairs of downward pointing legs, each of said pairs attaching at upper ends to a top cross bar, at least one leg of each pair being hingedly joined to at least one connecting bar;

a support platform, said support platform being pivotally attached to a bracket, said bracket being attached to said at least one connecting bar;

said platform having a first end for supporting a wrist of a stroke victim and a second end for supporting said antispasticity aid device, said second end having either of a hooking portion and a looping portion of a removable attachment device positioned upon an upper surface for removable attachment to said antispasticity aid device;

at least one elastic member, said elastic member being disposed between said bracket and an underside of said support platform; and said elastic member providing resistive stability for said platform when supporting a hand and arm of a stroke victim;

whereby, when a hand of a stroke victim is placed upon said hand-mounting member, said first restraining strap is disposed over said hand and through said first fastening slots, said length of said first restraining strap is adjusted to hold said hand in firm contact with said hand mounting member and when a thumb of stroke victim is placed upon said thumb-mounting member, said second restraining strap is disposed over said thumb and through said second fastening slots, said length of said second restraining strap is adjusted to hold said thumb in firm contact with said thumb mounting member, said thumb-mounting member is adjustable with respect to said hand-mounting member for comfort of said stroke victim.

55. An antispasticity aid device as claimed in claim 54 in which said thumb-mounting member is rotatably attached at its rear edge to said first side edge of said hand mounting member, permitting said thumb-mounting member to rotate through an arc in the plane of said hand mounting member.

56. A fifth accessory for use with either of said antispasticity aid device as described in claim 49 and said antispasticity aid device as described in claim 49 having a fixed thumb-mounting member, comprising:
- a floor bracket, said floor bracket having an upper surface, a lower surface, a pivotal mounting bracket affixed to said upper surface and a non-slip finish on said lower surface;
- an adjustable support shaft, said support shaft having an upper portion, a lower portion, said lower portion fitting slidably within said upper portion and having a clamping mechanism for adjustably fastening said upper portion to said lower portion at a variety of heights;
- said lower portion having a fitting affixed at a lower end, said fitting being sized and shaped to fit said pivotal mounting bracket;
- said upper portion having a handle at an upper end, said handle being sized and shaped to accept said mounting bracket of said antispasticity aid device; and
- whereby when said antispasticity aid device is removably affixed to said handle, a stroke victim will use said fifth accessory to exercise the arm and shoulder muscles.

57. An antispasticity aid device, comprising:
- a planar hand-mounting member, said hand-mounting member being formed of rigid material and being sized and shaped to extend beyond outer dimensions of a human hand without a thumb;
- said hand-mounting member having an upper surface, a lower surface, a front edge, a rear edge, a first side edge and a second side edge;
- said hand-mounting member having at least two first fastening slots disposed adjacent said first and second side edges, respectively;
- a first restraining strap, said first strap being sized and shaped to fit slidably through said first fastening slots and having a means for adjusting a length of said first strap;
- a thumb-mounting member, said thumb-mounting member being formed of rigid material and being sized and shaped to extend beyond outer dimensions of a human thumb;
- said thumb-mounting member having an upper surface, a lower surface, a front edge, a rear edge, a first side edge and a second side edge;
- said thumb-mounting member having at least two second fastening slots disposed adjacent said first and said second side edges of said thumb-mounting member, respectively;
- a second restraining strap, said second strap being sized and shaped to fit slidably through said second fastening slots and having a means for adjusting a length of said second strap;
- said thumb-mounting member being attached at its rear edge to said first side edge of said hand mounting member;
- either of a hooking portion and a looping portion of a removable attachment device, said portion being affixed to said lower surface of said planar hand-mounting member; and
- said portion providing a mechanism for removably attaching said antispasticity aid device to accessory devices;
- a sixth accessory comprising:
  - a support tab, said support tab having a first surface and a second surface, an aperture penetrating said first and second surfaces, either of a hooking portion and a looping portion of a removable attachment device affixed to one of said first and second surfaces;
  - said portion providing a mechanism for removably attaching said support tab to said antispasticity aid device;
  - an elastic chord, said elastic chord having a first end, a second end and being attached at said first end to said support tab through said aperture and having a mechanism at said second end for forming a loop adjacent said second end;
  - said loop serving to attach said elastic chord to a support fixture; and
- whereby, when said antispasticity aid device is attached to a hand of a stroke victim and said antispasticity aid device is attached to said support tab and said loop is attached to said fixture, said hand and arm of said stroke victim will be suspended for ease of washing; and
- whereby, when a hand of a stroke victim is placed upon said hand-mounting member, said first restraining strap is disposed over said hand and through said first fastening slots, said length of said first restraining strap is adjusted to hold said hand in firm contact with said hand mounting member and when a thumb of stroke victim is placed upon said thumb-mounting member, said second restraining strap is disposed over said thumb and through said second fastening slots, said length of said second restraining strap is adjusted to hold said thumb in firm contact with said thumb mounting member, said thumb-mounting member is adjustable with respect to said hand-mounting member for comfort of said stroke victim.

58. An antispasticity aid device as claimed in claim 55 in which said thumb-mounting member is rotatably attached at its rear edge to said first side edge of said hand mounting member, permitting said thumb-mounting member to rotate through an arc in the plane of said hand mounting member.

59. The sixth accessory, as described in claim 57, further comprising a weakened portion in said elastic chord, said weakened portion providing a safety feature for said stroke victim in the event said stroke victim should fall, the safety feature preventing said stroke victim from being suspended by said sixth accessory.

60. The sixth accessory, as described in claim 57, further comprising:
- a coupling in said elastic chord, said coupling having an attaching portion and a receiving portion;
- said attaching portion being affixed to an upper end of a lower portion of said elastic chord and having a head section and a reduced cross-section neck section disposed below said head section;
- said receiving portion being affixed to a lower end of an upper portion of said elastic chord having a cavity, said cavity being sized and shaped to frictionally fit over said attaching portion and having a resilient surrounding lower rim, said rim being sized and shaped to fit into said neck section; and whereby, when a downward pressure on said sixth accessory exceeds pressure required to locate said attaching portion in said receiving portion, said attaching portion and said receiving portions will separate, providing a safety feature for a stroke victim using said sixth accessory.

61. An antispasticity aid device, comprising:

a planar hand-mounting member, said hand-mounting member being formed of rigid material and being sized and shaved to extend beyond outer dimensions of a human hand without a thumb;

said hand-mounting member having an upper surface, a lower surface, a front edge, a rear edge, a first side edge and a second side edge;

said hand-mounting member having at least two first fastening slots disposed adjacent said first and second side edges, respectively;

a first restraining strap, said first strap being sized and shaped to fit slidably through said first fastening slots and having a means for adjusting a length of said first strap;

a thumb-mounting member, said thumb-mounting member being formed of rigid material and being sized and shaped to extend beyond outer dimensions of a human thumb;

said thumb-mounting member having an upper surface, a lower surface, a front edge, a rear edge, a first side edge and a second side edge;

said thumb-mounting member having at least two second fastening slots disposed adjacent said first and said second side edges of said thumb-mounting member, respectively;

a second restraining stray, said second strap being sized and shaped to fit slidably through said second fastening slots and having a means for adjusting a length of said second strap;

said thumb-mounting member being attached at its rear edge to said first side edge of said hand mounting member;

a seventh accessory comprising:
  a resilient arm support member, said arm support member having a first end, a second end and being formed into a loop, said loop being joined by an intermediate bridging member;
  said resilient arm member being sized and shaped to fit frictionally over a wheelchair arm and to provide a channel at an upper surface suitable for resting of a stroke victim's arm;
  at least one retaining strap, said retaining strap having a first portion and a second portion, each of said portions being attached to an outer edge of said loop and having either of a looping means and a hooking means attached to said portions to permit said retaining strap to be fastened over an arm of a stroke victim; and whereby, when a hand of a stroke victim is placed upon said hand-mounting member, said first restraining strap is disposed over said hand and through said first fastening slots, said length of said first restraining strap is adjusted to hold said hand in firm contact with said hand mounting member and when a thumb of stroke victim is placed upon said thumb-mounting member, said second restraining strap is disposed over said thumb and through said second fastening slots, said length of said second restraining strap is adjusted to hold said thumb in firm contact with said thumb mounting member, said thumb-mounting member is adjustable with respect to said hand-mounting member for comfort of said stroke victim.

62. An antispasticity aid device as claimed in claim 61 in which said thumb-mounting member is rotatably attached at its rear edge to said first side edge of said hand mounting member, permitting said thumb-mounting member to rotate through an arc in the plane of said hand mounting member.

63. The seventh accessory, as described in claim 61, further comprising a hand support platform, said hand support platform being attached to at least one end of said loop and being sized and shaped to fit beneath said antispasticity aid device, and having a series of slots for accepting retaining straps to hold said antispasticity aid device to said hand support platform.

64. An antispasticity aid device, comprising:

a planar hand-mounting member, said hand-mounting member being formed of rigid material and being sized and shaped to extend beyond outer dimensions of a human hand without a thumb;

said hand-mounting member having an upper surface, a lower surface, a front edge, a rear edge, a first side edge and a second side edge;

said hand-mounting member having at least two first fastening slots disposed adjacent said first and second side edges, respectively;

a first restraining strap, said first strap being sized and shaped to fit slidably through said first fastening slots and having a means for adjusting a length of said first strap;

a thumb-mounting member, said thumb-mounting member being formed of rigid material and being sized and shape d to extend beyond outer dimensions of a human thumb;

said thumb-mounting member having an upper surface, a lower surface, a front edge, a rear edge, a first side edge and a second side edge;

said thumb-mounting member having at least two second fastening slots disposed adjacent said first and said second side edges of said thumb-mounting member, respectively;

a second restraining strap, said second strap being sized and shaped to fit slidably through said second fastening slots and having a means for adjusting a length of said second strap;

said thumb-mounting member being attached at its rear edge to said first side edge of said hand mounting member;

either of a hooking portion and a looping portion of a removable attachment device, said portion being affixed to said lower surface of said planar hand-mounting member; and said portion providing a mechanism for removably attaching said antispasticity aid device to accessory devices;

an eighth accessory comprising:
  a vertically oriented mounting structure, said mounting structure having an upper end, a lower end, a support base disposed at said lower end and a central adjusting tract;
  a bearing mount, said bearing mount being slidably affixed to said central adjusting track and having a curved exterior edge;
  a bearing, said bearing being affixed to a center of said bearing mount;

a planar positioning member, said positioning member having a perimeter, a front surface, a rear surface and being affixed to said bearing at a center portion of said rear surface;

a planar, L-shaped control bracket, said control bracket being pivotally mounted adjacent a corner of said L-shape to said front surface of said positioning member adjacent said perimeter, and having a control bracket bearing mounted at one end of said L-shape;

at least one stop pin, said stop pin being mounted to said front surface of said positioning member and being disposed between arms of said L-shaped control bracket;

an antispasticity aid support member, said support member having an upper surface and a lower surface, being pivotally mounted to said control bracket bearing, being sized and shaped to support said stroke victim aid, and having either of a hooking portion and a looping portion of a removable attachment device affixed to said upper surface of said support member for attachment to said antispasticity aid device;

a first elastic member, said first elastic member having a first end and a second end and being attached at said first end to said rear surface of said planar positioning member adjacent said perimeter and being attached at said second end to said curved exterior edge of said bearing mount; and whereby, when said antispasticity aid device is attached to a hand of a stroke victim and said antispasticity aid device is attached to said support member, said eighth accessory will provide a mechanism for exercising arm muscles of said stroke victim, permitting rising extension of said arm muscles; and whereby, when a hand of a stroke victim is placed upon said band-mounting member, said first restraining strap is disposed over said hand and through said first fastening slots, said length of said first restraining strap is adjusted to hold said hand in firm contact with said hand mounting member and when a thumb of stroke victim is placed upon said thumb-mounting member, said second restraining strap is disposed over said thumb and through said second fastening slots, said length of said second restraining strap is adjusted to hold said thumb in firm contact with said thumb mounting member, said thumb-mounting member is adjustable with respect to said hand-mounting member for comfort of said stroke victim.

65. An antispasticity aid device as claimed in claim 64 in which said thumb-mounting member is rotatably attached at its rear edge to said first side edge of said hand mounting member, permitting said thumb-mounting member to rotate through an arc in the plane of said hand mounting member.

66. The eighth accessory, as described in claim 64, further comprising a second elastic member, said second elastic member having a first end and a second end and being attached at said first end to said front surface of said planar positioning member inward from said perimeter and being attached at said second end to said support member, thereby providing additional stability for said arm of said stroke victim as said eighth accessory is used for exercising said arm of said stroke victim.

67. An antispasticity aid device, comprising:

a planar hand-mounting member, said hand-mounting member being formed of rigid material and being sized and shaped to extend beyond outer dimensions of a human hand without a thumb;

said hand-mounting member having an upper surface, a lower surface, a front edge, a rear edge, a first side edge and a second side edge;

said hand-mounting member having at least two first fastening slots disposed adjacent said first and second side edges, respectively;

a first restraining strap, said first strap being sized and shaped to fit slidably through said first fastening slots and having a means for adjusting a length of said first strap;

a thumb-mounting member, said thumb-mounting member being formed of rigid material and being sized and shaped to extend beyond outer dimensions of a human thumb;

said thumb-mounting member having an upper surface, a lower surface, a front edge, a rear edge, a first side edge and a second side edge;

said thumb-mounting member having at least two second fastening slots disposed adjacent said first and said second side edges of said thumb-mounting member, respectively;

a second restraining strap, said second strap being sized and shaped to fit slidably through said second fastening slots and having a means for adjusting a length of said second strap;

said thumb-mounting member being attached at its rear edge to said first side edge of said hand mounting member;

a ninth accessory comprising:

a support platform, said support platform being formed of planar semi-rigid, resilient material, having a hand-support section and an arm support section, and being attached to a wheelchair;

said hand support section having a distal end and a proximate end and being sized and shaped to support said antispasticity aid device;

said arm support section having a first section and a second section, said first section having a first end and a second end, said second section having a first end and a second end, and said first section of said arm support section being attached at said first end to said proximate end of said hand support section;

an elastic element, said elastic element having a front end and a rearward end, said front end of said elastic element being attached to said second end of said first section of said arm support section, and said rearward end of said elastic element being attached to said first end of said second section of said arm support section;

whereby, when said ninth accessory is attached to said antispasticity aid device and said antispasticity aid device is attached to the hand of a stroke victim, said ninth accessory will permit said stroke victim to apply force against said elastic element to provide physical therapy for arm muscles of said stroke victim; and whereby, when a hand of a stroke victim is placed upon said hand-mounting member, said first restraining strap is disposed over said hand and through said first fastening slots, said length of said first restraining strap is adjusted to hold said hand in firm contact with said hand mounting member and when a thumb of stroke victim is placed upon said thumb-mounting member, said second restraining strap is disposed over said thumb and through said second fastening slots, said length of said second restraining strap is adjusted to hold said thumb in firm contact with said thumb mounting member, said thumb-mounting member is adjustable with respect to said hand-mounting member for comfort of said stroke victim.

68. An antispasticity aid device as claimed in claim 67 in which said thumb-mounting member is rotatably attached at its rear edge to said first side edge of said hand mounting member, permitting said thumb-mounting member to rotate through an arc in the plane of said hand mounting member.

69. The ninth accessory as described in claim 67, further comprising a means for attaching said front end of said elastic element to said second end of said first section of said arm support section and said rearward end of said elastic element to said first end of said second section of said arm support section.

70. The ninth accessory as described in claim 69, wherein the means for attaching said front end of said elastic element to said second end of said first section of said arm support section and said rearward end of said elastic element to said first end of said second section of said arm support section further comprise:
 at least one bracket, said bracket having a first end and a second end, and being attached to either of said second end of said first section of said arm support section and said first section of said second section of said arm support section to said first end of said bracket.

71. The ninth accessory as described in claim 67, further comprising an extension spring, said extension spring having a front end and a rearward end, and said front end of said extension spring being attached to said second end of said first section of said arm support section, and said rearward end of said extension spring being attached to said first end of said second section of said arm support section.

72. The ninth accessory as described in claim 67, further comprising a mechanism of attaching said support platform at said second end of said second section of said arm support section to a hollow tube at the rear of said wheelchair.

73. An antispasticity aid device, comprising:
 a planar hand-mounting member, said hand-mounting member being formed of rigid material and being sized and shaped to extend beyond outer dimensions of a human hand without a thumb;
 said hand-mounting member having an upper surface, a lower surface, a front edge, a rear edge, a first side edge and a second side edge;
 said hand-mounting member having at least two first fastening slots disposed adjacent said first and second side edges, respectively;
 a first restraining strap, said first strap being sized and shaped to fit slidably through said first fastening slots and having a means for adjusting a length of said first strap;
 a thumb-mounting member, said thumb-mounting member being formed of rigid material and being sized and shaped to extend beyond outer dimensions of a human thumb;
 said thumb-mounting member having an upper surface, a lower surface, a front edge, a rear edge, a first side edge and a second side edge;
 said thumb-mounting member having at least two second fastening slots disposed adjacent said first and said second side edges of said thumb-mounting member, respectively;
 a second restraining strap, said second strap being sized and shaped to fit slidably through said second fastening slots and having a means for adjusting a length of said second strap;
 said thumb-mounting member being rotatably attached at its rear edge to said first side edge of said hand mounting member, permitting said thumb-mounting member to rotate through an arc in the plane of said hand mounting member; said thumb-mounting member being lockable in a plurality of positions about a point where it is rotatably attached at its rear edge to said first side edge of said hand-mounting member
 a plurality of detents, said detents being disposed at said rear edge of said thumb-mounting member;
 a ball channel, said ball channel being disposed in either of said first side edge and said second side edge of said hand-mounting member, and having a compression spring disposed within said channel;
 a positioning ball, said ball being sized and shaped to fit slidably within said channel and to fit within said detents, said ball being maintained in one of said detents by said compression spring; and
 whereby, when pressure is applied to a side edge of said thumb mounting member, said ball will be moved from one detent to the next, said compression spring tending to maintain a position of said thumb mounting member with respect to said hand mounting member; and
 whereby, when a hand of a stroke victim is placed upon said hand-mounting member, said first restraining strap is disposed over said hand and through said first fastening slots, said length of said first restraining strap is adjusted to hold said hand in firm contact with said hand mounting member and when a thumb of stroke victim is placed upon said thumb-mounting member, said second restraining strap is disposed over said thumb and through said second fastening slots, said length of said second restraining strap is adjusted to hold said thumb in firm contact with said thumb mounting member, said thumb-mounting member is adjustable with respect to said hand-mounting member for comfort of said stroke victim.

* * * * *

Disclaimer

6,949,077 — Robert K. Froom, Gardena, CA (US). ANTISPASTICITY AID DEVICE AND RELATED ACCESSORIES. Patent dated September 27, 2005. Disclaimer filed November 12, 2008, by the inventor, Robert K. Froom.

Hereby completely disclaims all of the claims of said patent.

(*Official Gazette, September 22, 2009*)